US011912782B2

(12) United States Patent
Kinneer et al.

(10) Patent No.: US 11,912,782 B2
(45) Date of Patent: Feb. 27, 2024

(54) BCMA MONOCLONAL ANTIBODY-DRUG CONJUGATE

(71) Applicant: MedImmune, LLC, Gaithersburg, MD (US)

(72) Inventors: Krista Kinneer, Gaithersburg, MD (US); Reena Varkey, Gaithersburg, MD (US); Xiaodong Xiao, Frederick, MD (US); Elaine M. Hurt, Gaithersburg, MD (US); David Tice, Gaithersburg, MD (US)

(73) Assignee: MedImmune, LLC, Gaithersburg, MD (US)

(*) Notice: Subject to any disclaimer, the term of this patent is extended or adjusted under 35 U.S.C. 154(b) by 366 days.

(21) Appl. No.: 17/215,479

(22) Filed: Mar. 29, 2021

(65) Prior Publication Data
US 2021/0214460 A1 Jul. 15, 2021

Related U.S. Application Data

(62) Division of application No. 16/050,944, filed on Jul. 31, 2018, now Pat. No. 10,988,546.

(60) Provisional application No. 62/596,194, filed on Dec. 8, 2017, provisional application No. 62/539,825, filed on Aug. 1, 2017.

(51) Int. Cl.
| | | |
|---|---|---|
| *C07K 16/30* | (2006.01) | |
| *C07K 16/28* | (2006.01) | |
| *A61K 47/68* | (2017.01) | |
| *A61P 35/00* | (2006.01) | |
| *A61K 31/202* | (2006.01) | |
| *A61K 31/4741* | (2006.01) | |
| *A61K 31/551* | (2006.01) | |
| *A61K 31/7048* | (2006.01) | |
| *C12N 15/62* | (2006.01) | |
| *A61K 39/00* | (2006.01) | |

(52) U.S. Cl.
CPC ........ *C07K 16/3061* (2013.01); *A61K 31/202* (2013.01); *A61K 31/4741* (2013.01); *A61K 31/551* (2013.01); *A61K 31/7048* (2013.01); *A61K 47/6803* (2017.08); *A61K 47/6849* (2017.08); *A61K 47/6867* (2017.08); *A61P 35/00* (2018.01); *C07K 16/2878* (2013.01); *C12N 15/62* (2013.01); *A61K 2039/505* (2013.01); *C07K 2317/21* (2013.01); *C07K 2317/33* (2013.01); *C07K 2317/73* (2013.01); *C07K 2317/77* (2013.01); *C07K 2317/92* (2013.01)

(58) Field of Classification Search
CPC ............ A61K 47/6867; A61K 47/6803; A61K 47/6849; A61K 2039/505
See application file for complete search history.

(56) References Cited

U.S. PATENT DOCUMENTS

| | | | |
|---|---|---|---|
| 10,988,546 B2* | 4/2021 | Kinneer | ............ A61K 31/7048 |
| 2022/0218835 A1* | 7/2022 | Kinneer | ............ A61K 47/6849 |

FOREIGN PATENT DOCUMENTS

| | | |
|---|---|---|
| WO | 2010104949 A2 | 9/2010 |
| WO | 2012163805 A1 | 12/2012 |
| WO | 2013154760 A1 | 10/2013 |
| WO | 2014089335 A2 | 6/2014 |
| WO | 2016166629 A1 | 10/2016 |

OTHER PUBLICATIONS

KInneer et al (Clin Cancer Res; 24(24) Dec. 15, 2018).*
Xing et al (Clin Cancer Res 2021;27:5376-88).*
Ryan, et al., "Antibody targeting of B-cell maturation antigen on malignant plasma cells", Mol Cancer Ther., 2007, vol. 6(11), pp. 3009-3018.
Cohen, et al., "First in Human Study with GSK2857916, an Antibody Drug Conjugated to Microtubule-Disrupting Agent Directed Against B-Cell Maturation Antigen (BCMA) in Patients with Relapsed/Refractory Multiple Myeloma (MM): Results from Study BMA117159 Part 1 Dose Escalation", Blood, 2016, vol. 128:1148, pp. 1-4.
Kinneer, et al., "Preclinical Evaluation of MEDI2228, a BCMA-Targeting Pyrrolobenzodiazepine-Linked Antibody Drug Conjugate for the Treatment of Multiple Myeloma", Blood, 2017, vol. 130:S1:3153, pp. 1-8.
Ko, et al., "Preclinical Evaluation of Hdp-101, a Novel Anti-BCMA Antibody-Drug Conjugate, in Multiple Myeloma", Blood, 2017, vol. 130:S1:3070, pp. 1-8.
MedImmune LLC, et al., "MEDI2228 in Subjects With Relapsed/Refractory Multiple Myeloma (MEDI2228)", ClinicalTrials.gov Identifier NCT03489525, 2018, pp. 1-10.

* cited by examiner

*Primary Examiner* — Lynn A Bristol

(57) ABSTRACT

The disclosure is directed to an antibody-drug conjugate (ADC) comprising a monoclonal antibody, or an antigen-binding fragment thereof, directed against B-cell maturation antigen (BCMA) conjugated to a cytotoxin. The disclosure also provides compositions comprising the antibody-drug conjugate and methods of killing multiple myeloma cells (including multiple myeloma stems cells) that express BCMA by contacting multiple myeloma cells with the ADC.

19 Claims, 19 Drawing Sheets
Specification includes a Sequence Listing.

FIG. 13
15B2 GL 60nM
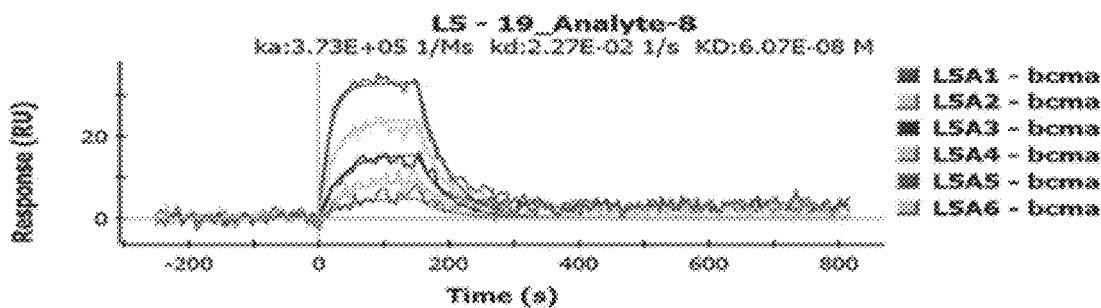
I09 9.8 nM
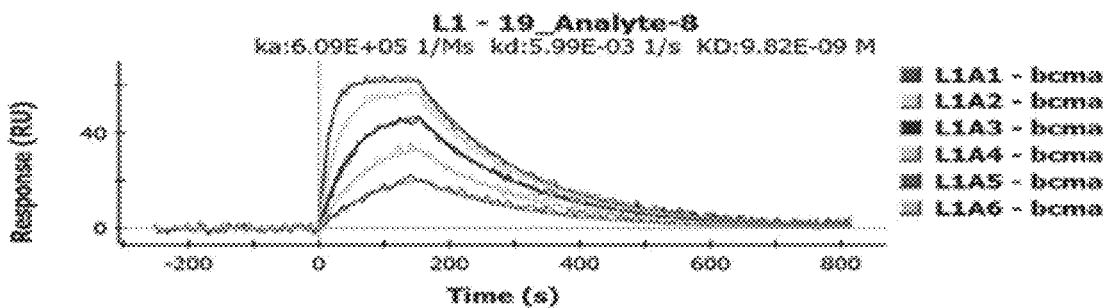
P10 5.3 nM
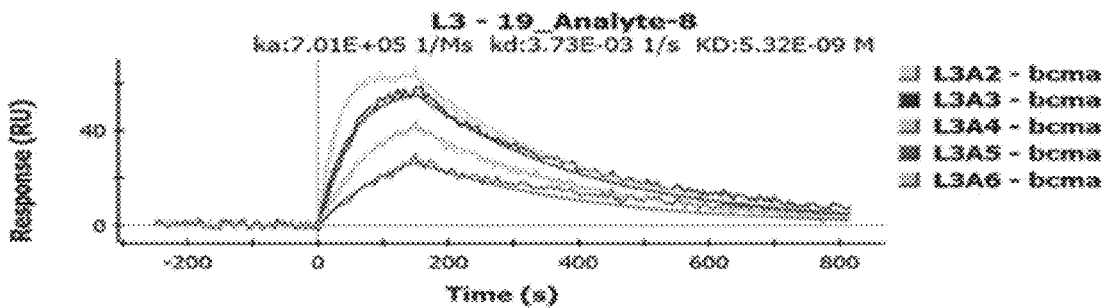
L15 4.5 nM
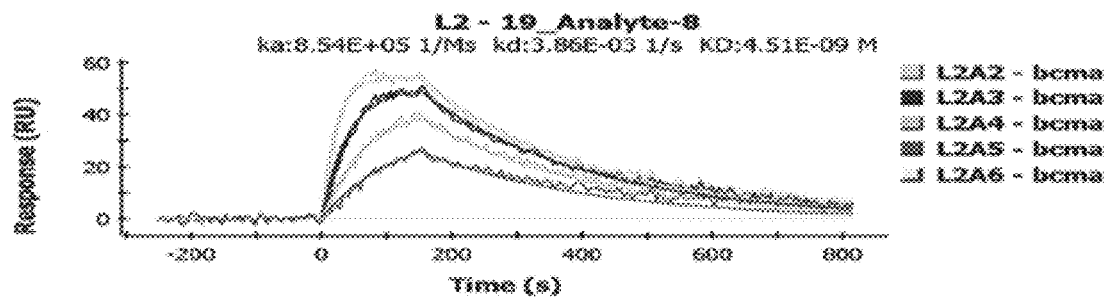

FIG. 15
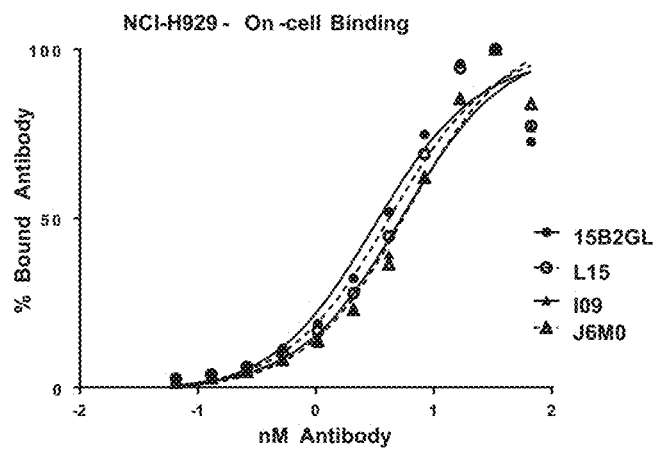
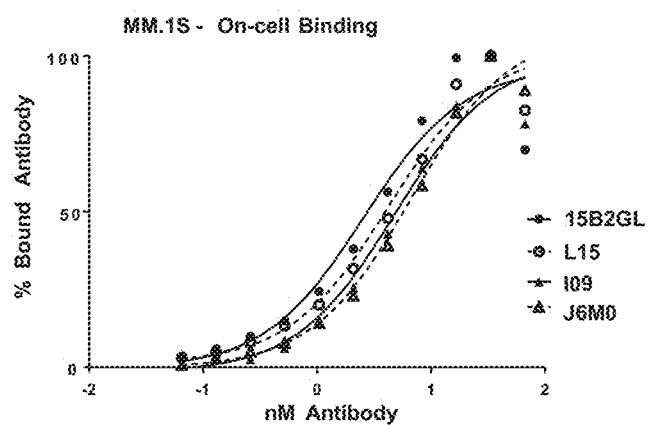
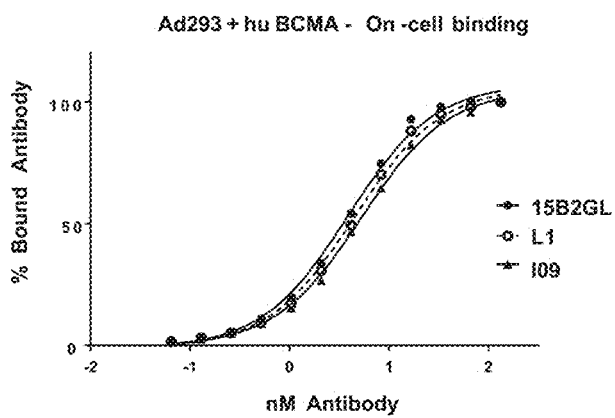

BCMA MONOCLONAL ANTIBODY-DRUG CONJUGATE

CROSS-REFERENCE TO RELATED APPLICATIONS

This application is a Divisional of U.S. application Ser. No. 16/050,944 filed on Jul. 31, 2018, said application Ser. No. 16/050,944 claims benefit under 35 U.S.C. § 119(e) of the following U.S. Provisional Application Nos. 62/596,194 filed Dec. 8, 2017 and 62/539,825 filed Aug. 1, 2017. Each of the above listed applications is incorporated by reference herein in its entirety for all purposes.

INCORPORATION-BY-REFERENCE OF MATERIAL SUBMITTED ELECTRONICALLY

This application includes a Sequence Listing submitted electronically entitled "BCMA-100-US-DIV_ST25.txt", created on Mar. 17, 2021 and having a size of 16,537 bytes, which is hereby incorporated by reference in its entirety.

BACKGROUND

Multiple myeloma (MM) is a malignancy characterized by an accumulation of clonal plasma cells (see, e.g., Palumbo et al., *New England J. Med.*, 364(11): 1046-1060 (2011), and Lonial et al., *Clinical Cancer Res.*, 77(6): 1264-1277 (2011)). Current therapies for MM include chemotherapy, radiation, surgery, biophosphonates, and autologous stem-cell transplantation (ASCT). While these therapies often cause remissions, nearly all patients eventually relapse and die (see, e.g., Lonial et al., supra, and Rajkumar, *Nature Rev. Clinical Oncol*, 5(8): 479-491 (2011)).

B-cell maturation antigen (BCMA) is a tumor necrosis family receptor (TNFR) member expressed on cells of the B-cell lineage (Laabi et al., *Nucleic Acids Research*, 22(7): 1147-1154 (1994)). BCMA expression is highest on terminally differentiated B cells. BCMA is involved in mediating the survival of plasma cells for maintaining long-term humoral immunity. The expression of BCMA has been linked to a number of cancers, autoimmune disorders, and infectious diseases. BCMA RNA has been detected universally in multiple myeloma cells, and BCMA protein has been detected on the surface of plasma cells from multiple myeloma patients by several investigators (see, e.g., Novak et al, *Blood,* 103(2): 689-694 (2004); Neri et al., *Clinical Cancer Research,* 73(19): 5903-5909 (2007); Bellucci et al., *Blood,* 105(10): 3945-3950 (2005); and Moreaux et al., *Blood,* 703(8): 3148-3157 (2004)). As such, BCMA has been investigated as a possible therapeutic target for multiple myeloma.

There remains a need for compositions that can be used in methods to treat multiple myeloma. This invention provides such compositions and methods.

BRIEF SUMMARY OF THE INVENTION

The disclosure provides an antibody-drug conjugate (ADC) comprising a monoclonal antibody, or an antigen-binding fragment thereof, directed against B-cell maturation antigen (BCMA) conjugated to a cytotoxin. The monoclonal antibody comprises (a) a heavy chain variable region comprising a complementarity determining region 1 (HCDR1) amino acid sequence of SEQ ID NO: 1, an HCDR2 amino acid sequence of SEQ ID NO: 2, and an HCDR3 amino acid sequence of SEQ ID NO: 3 and (b) a light chain variable region comprising a complementarity determining region 1 (LCDR1) amino acid sequence of SEQ ID NO: 4, an LCDR2 amino acid sequence of SEQ ID NO: 5, and an LCDR3 amino acid sequence of SEQ ID NO: 6.

In addition, the disclosure provides compositions comprising the foregoing antibody-drug conjugate, and methods of killing multiple myeloma cells (including multiple myeloma stem cells) that express BCMA by contacting multiple myeloma cells with the ADC.

The disclosure also provides a monoclonal antibody, or an antigen-binding fragment thereof, directed against BCMA which comprises (a) a heavy chain variable region comprising a complementarity determining region 1 (HCDR1) amino acid sequence of SEQ ID NO: 1, an HCDR2 amino acid sequence of SEQ ID NO: 2, and an HCDR3 amino acid sequence of SEQ ID NO: 3 and (b) a light chain variable region comprising a complementarity determining region 1 (LCDR1) amino acid sequence of SEQ ID NO: 4, an LCDR2 amino acid sequence of SEQ ID NO: 5, and an LCDR3 amino acid sequence of SEQ ID NO: 6.

BRIEF DESCRIPTION OF THE SEVERAL VIEWS OF THE DRAWING(S)

FIG. 2 are graphs illustrating the ability of BCMA antibody drug-conjugates to kill multiple myeloma (MM) and plasma cell leukemia (PCL) cells in vitro, as described in Example 4. FIG. 2A-2H show viability of specific BCMA-expressing multiple myeloma and plasma cell leukemia cell lines treated with the indicated ADCs, while FIGS. 21 and 2J show viability of cell lines that do not express BCMA.

Figure 3A:
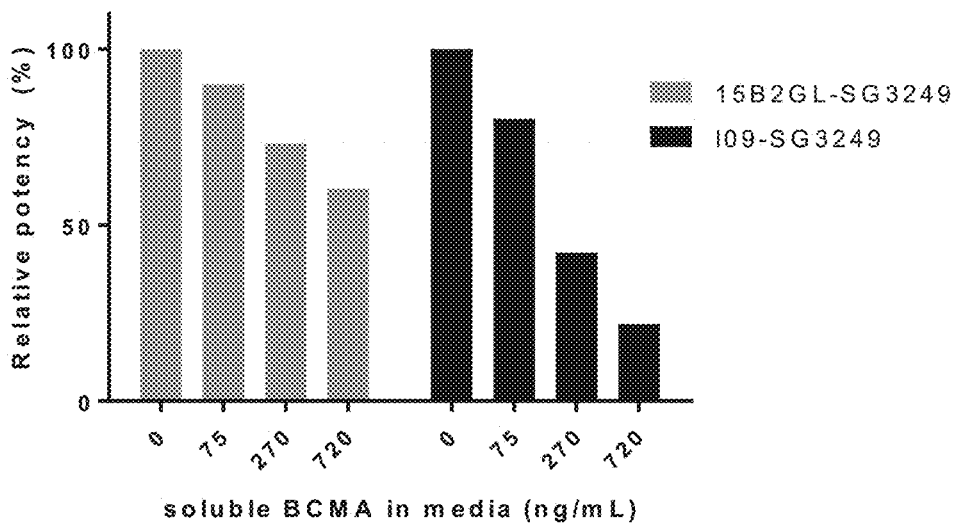
Figure 3B:
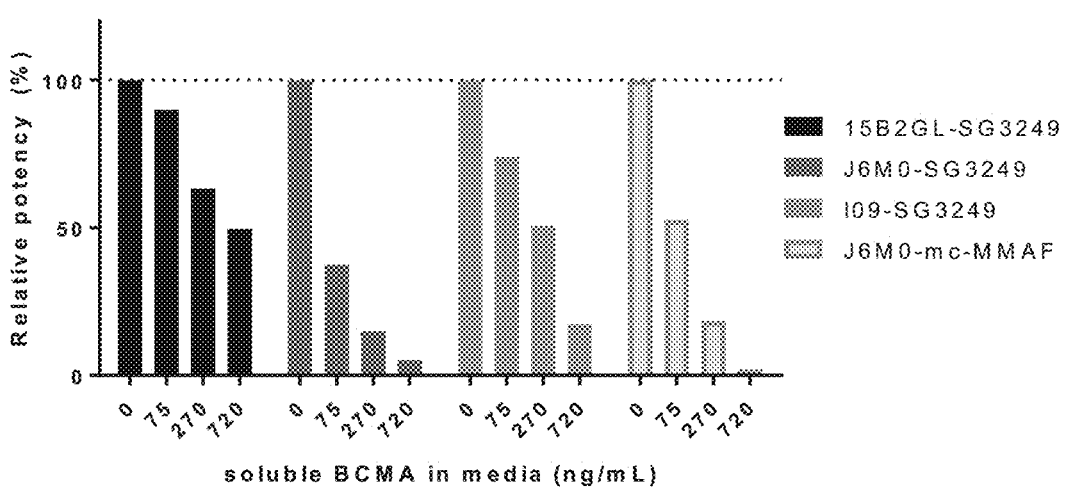

FIG. 3 contains graphs illustrating the killing of multiple myeloma cell lines in the presence of soluble BCMA by the antibody drug conjugate 15B2GL-SG3249 as compared to the ADC 109-5G3249 in conditioned media collected from Ad293 cells expressing human BCMA (FIG. 3A) or as compared to the ADCs J6M0-mc-MMAF and J6M0-SG3249 in conditioned media collected from Ad293 cells expressing human BCMA (FIG. 3B), as described in Example 4.

Figure 4:
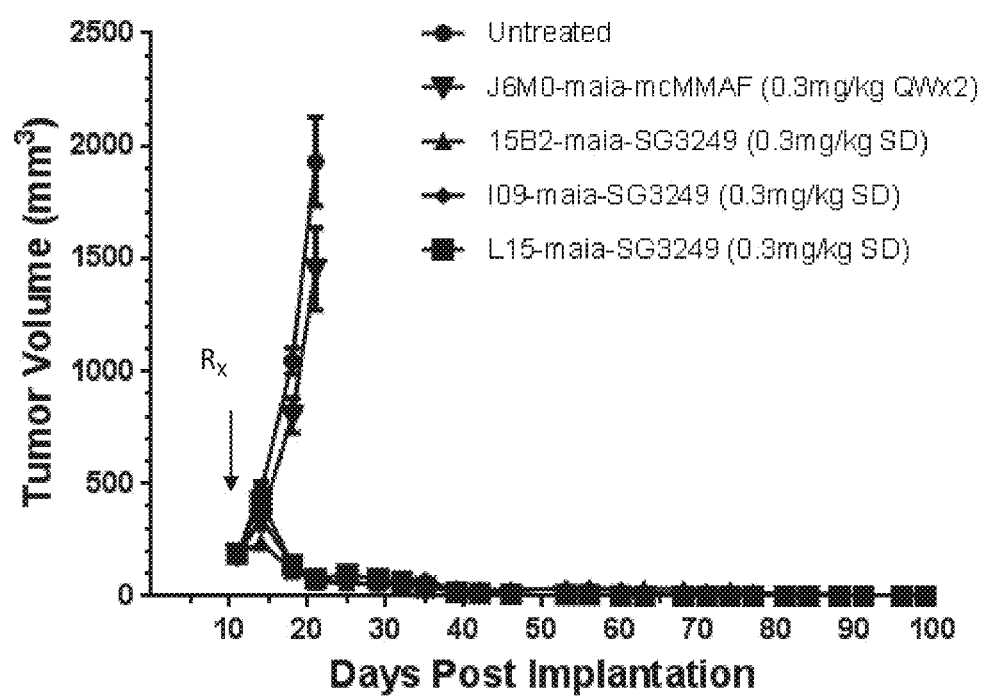

FIG. 4 is a graph illustrating change in tumor volume in a H929 xenograft mouse model of multiple myeloma in response to treatment with BCMA-targeting ADCs 15B2GL-SG3249, 109-5G3249, L15-SG3249, and J6M0-mc-MMAF as compared to untreated mice.

Figure 5:
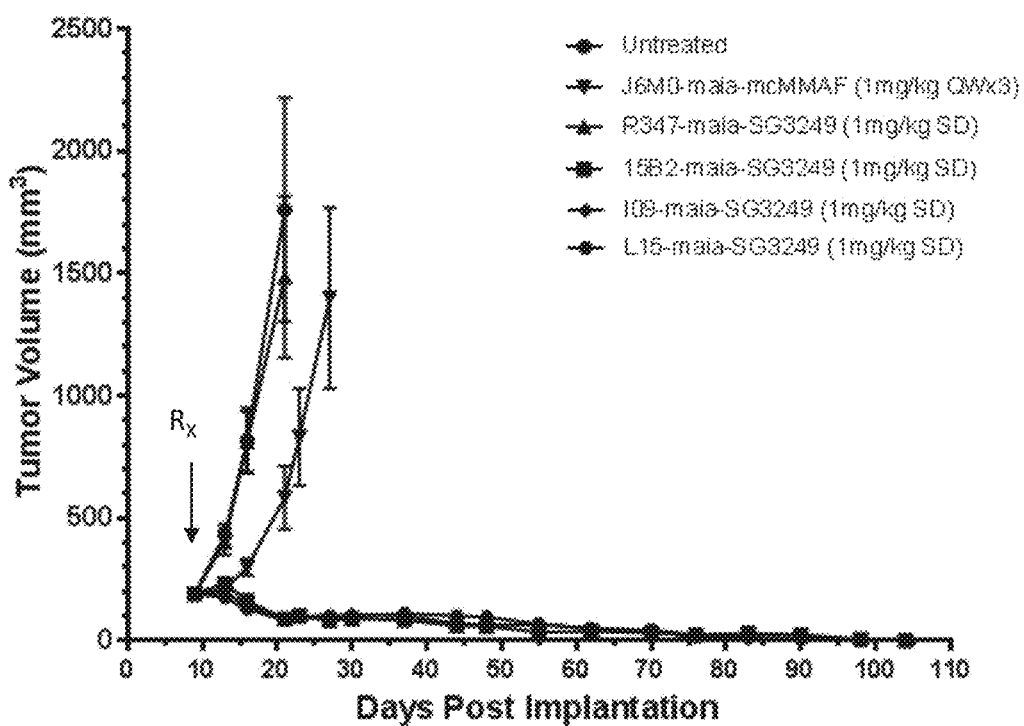

FIG. 5 is a graph illustrating change in tumor volume in a JJN3 xenograft mouse model of multiple myeloma in response to treatment with ADCs 15B2GL-SG3249, 109-5G3249, L15-SG3249, J6M0-mc-MMAF, and isotype control IgG1-SG3249 as compared to untreated mice.

Figure 6:
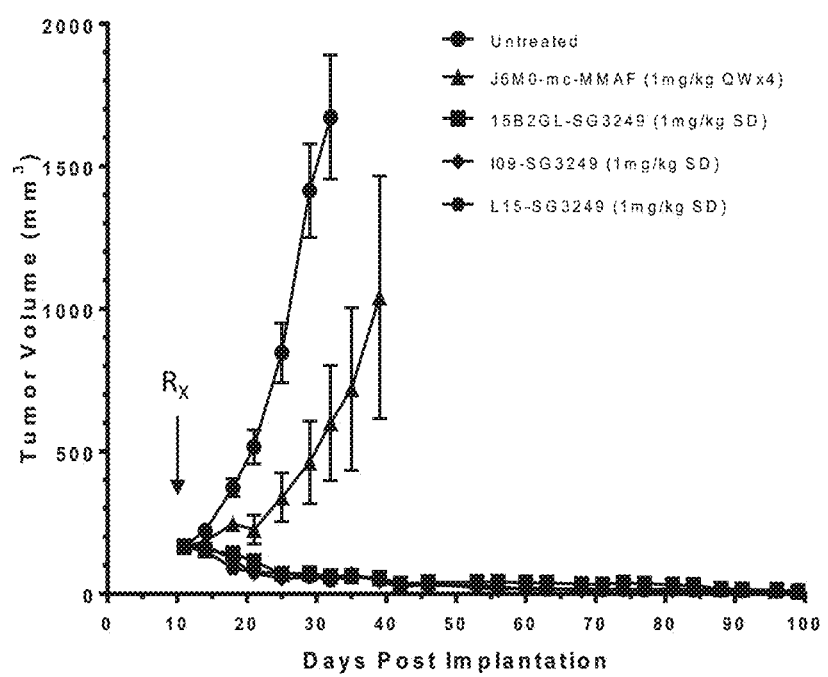

FIG. 6 is a graph illustrating change in tumor volume in a MM.1S xenograft mouse model of plasma cell leukemia in response to treatment with ADCs 15B2GL-SG3249, 109-SG3249, L15-SG3249, and J6M0-mc-MMAF as compared to untreated mice.

Figure 7:
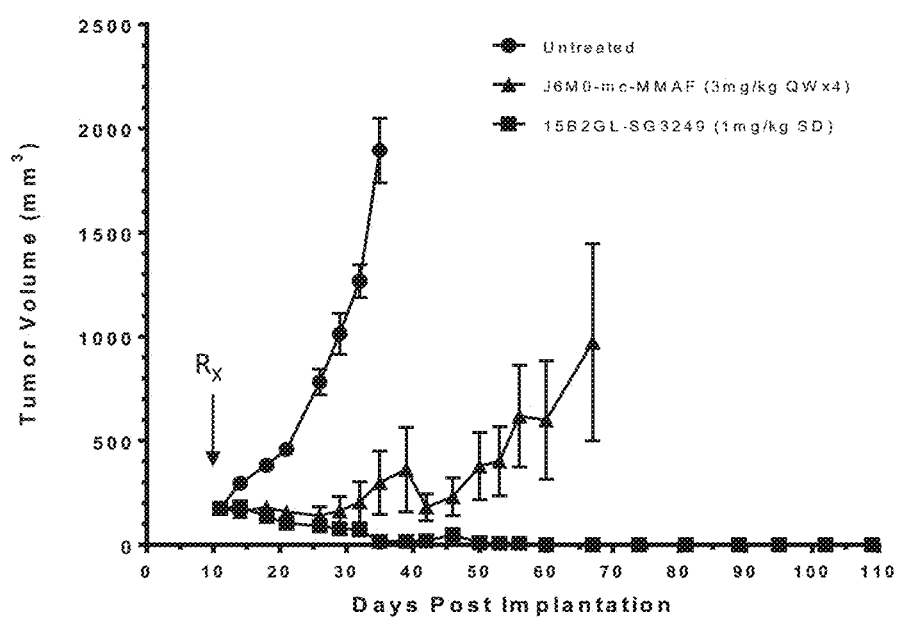

FIG. 7 is a graph illustrating change in tumor volume in a MM.1R xenograft mouse model of plasma cell leukemia in response to treatment with ADCs 15B2GL-SG3249 and J6M0-mc-MMAF as compared to untreated mice.

Figure 8:
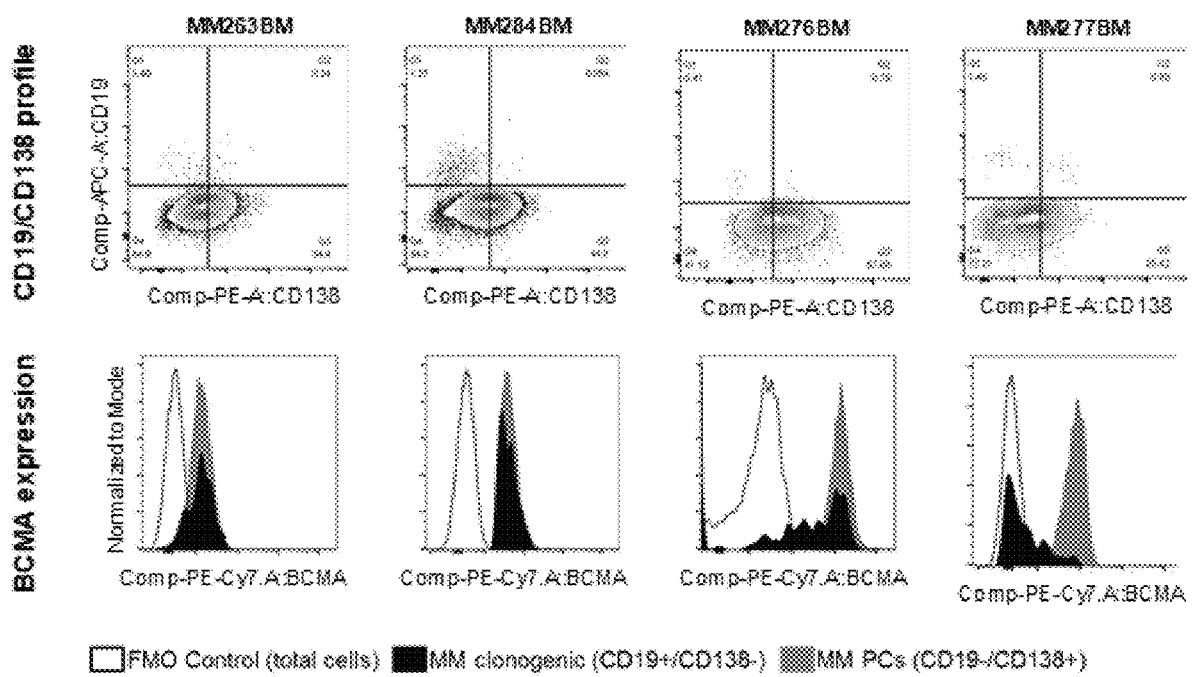
Figure 9A:
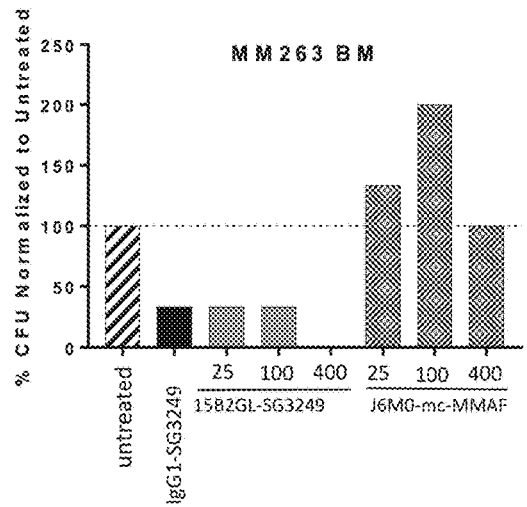
Figure 9B:
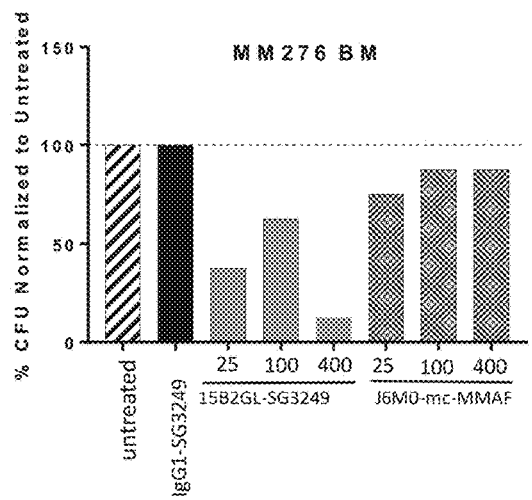
Figure 9C:
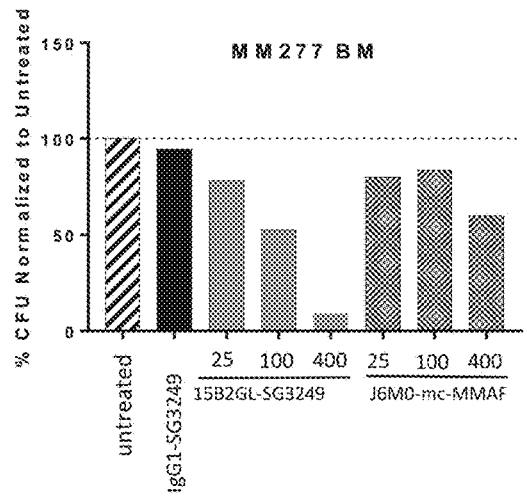
Figure 9D:
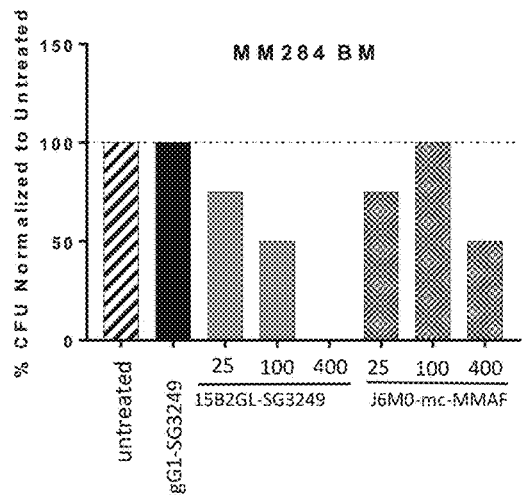
Figure 10A:
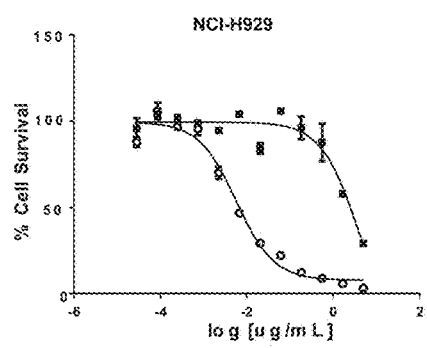
Figure 10B:
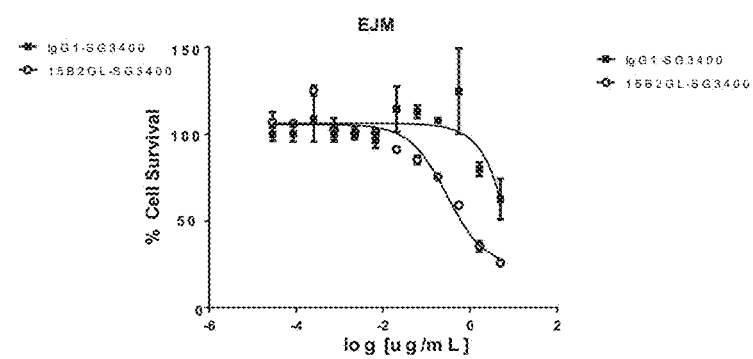
Figure 10C:
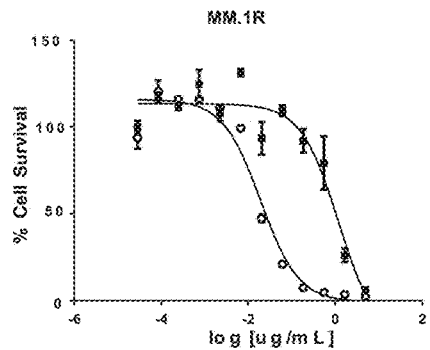
Figure 10D:
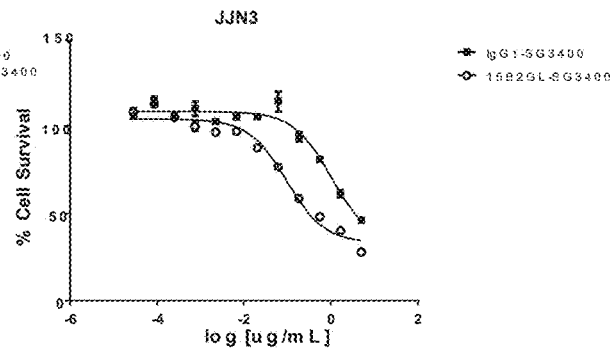
Figure 10E:
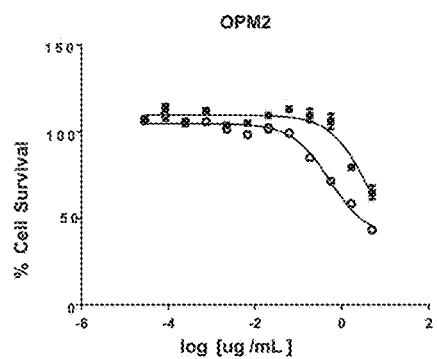
Figure 10F:
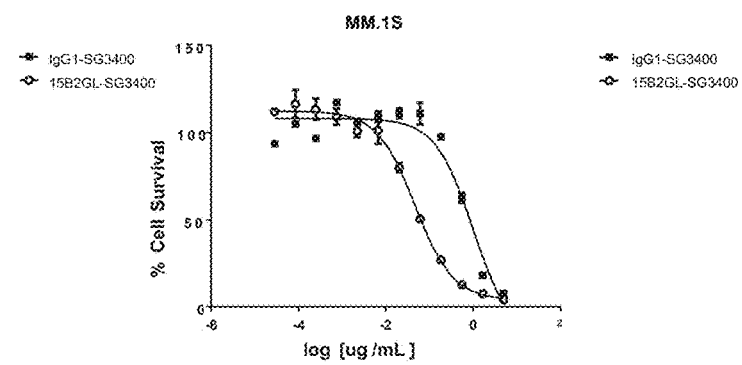
Figure 10G:
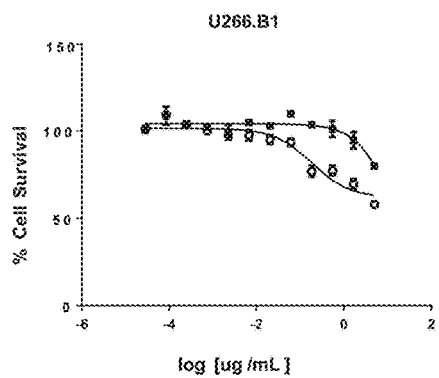
Figure 10H:
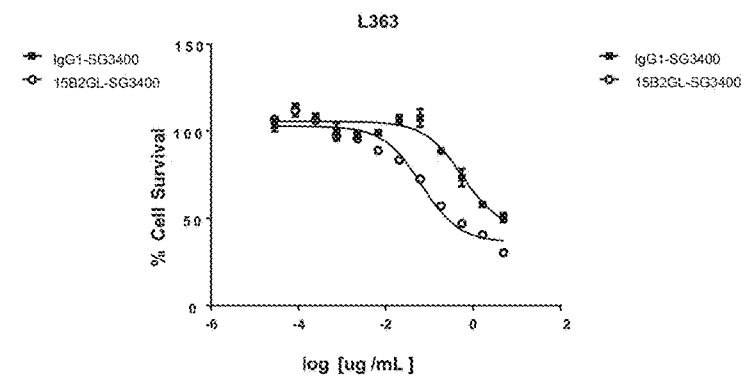
Figure 10I:
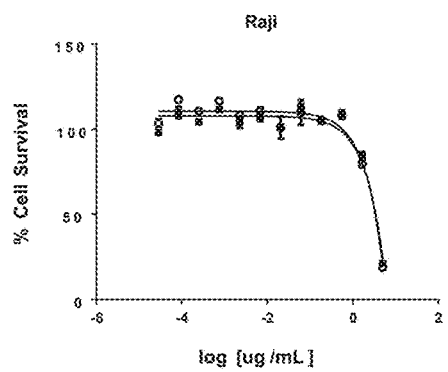
Figure 10J:
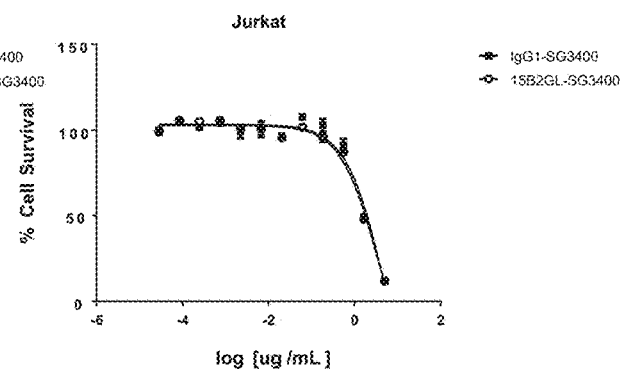

FIG. 8 contains a series of graphs and flow cytometry plots which illustrate expression of BCMA on MM stem cells. BCMA expression was detected on both the MM plasma cells (CD19-CD138+, grey trace) and on MM stem cells (CD19+CD138-, black trace).

FIG. 9 contain a series of graphs illustrating the sensitivity of MM stem cells from patients samples MM263 (FIG. 9A), MM276 (FIG. 9B), MM277 (FIG. 9C), and MM284 (FIG. 9D) to the ADC 15B2GL-SG3249 as compared to the ADC J6M0-mc-MMAF in a clonogenic assay. Controls include untreated cells and a non-specific IgG1-SG3249 conjugate at the highest dose of 400 ng per mL. The number of colonies formed was normalized to the number formed in the untreated culture, which was set to 100%.

FIG. 10 are graphs illustrating the ability of a BCMA antibody drug-conjugate to kill multiple myeloma (MM) and plasma cell leukemia (PCL) cells in vitro, as described in Example 7. FIG. 10A-10H show viability of specific BCMA-expressing multiple myeloma and plasma cell leukemia cell lines treated with the indicated ADC, while FIGS. 101 and 10J show viability of cell lines that do not express BCMA.

Figure 11:
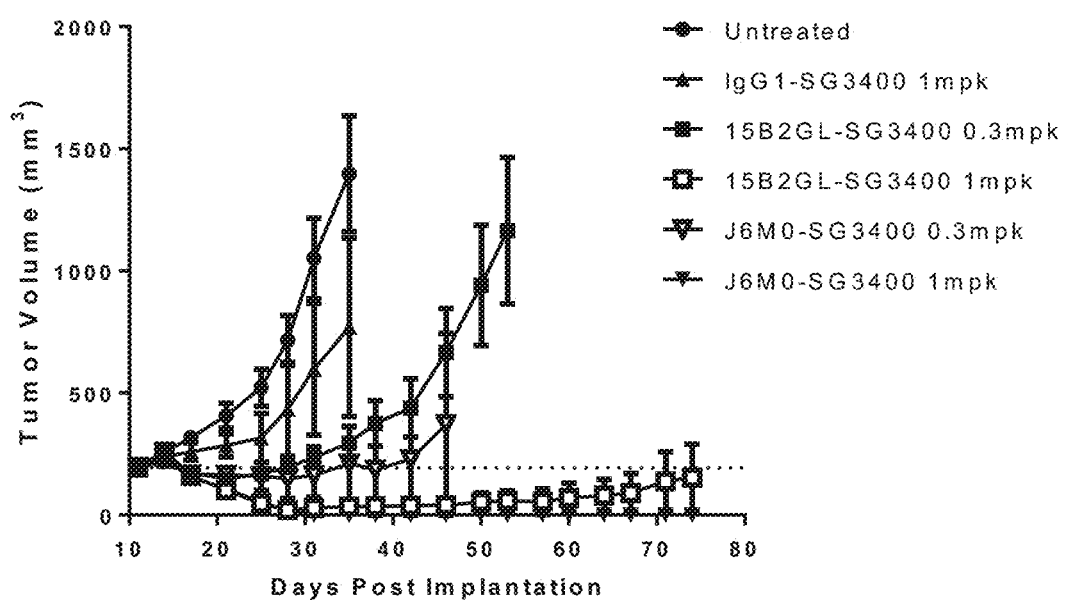

FIG. 11 is a graph illustrating change in tumor volume in a H929 xenograft mouse model of multiple myeloma in response to treatment with BCMA-targeting ADCs 15B2GL-SG3400, J6M0-SG3400, and isotype control IgG1-SG3400 as compared to untreated mice.

Figure 12:
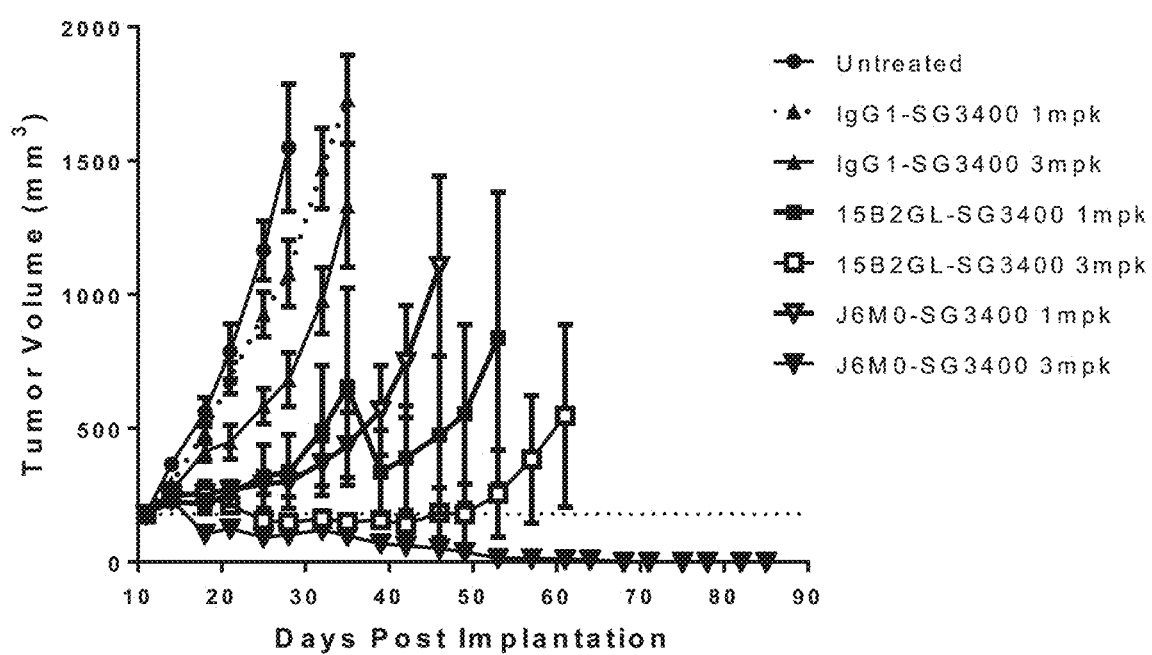

FIG. 12 is a graph illustrating change in tumor volume in a MM.1S xenograft mouse model of plasma cell leukemia in response to treatment with BCMA-targeting ADCs 15B2GL-SG3400, J6M0-SG3400, and isotype control IgG1-SG3400 as compared to untreated mice.

FIG. 13 are graphs illustrating the affinity and kinetics measurements of 15B2GL, 109, P10, and L15 antibody binding to human BCMA using a SPR-based ProteOn™ system.

Figure 14:
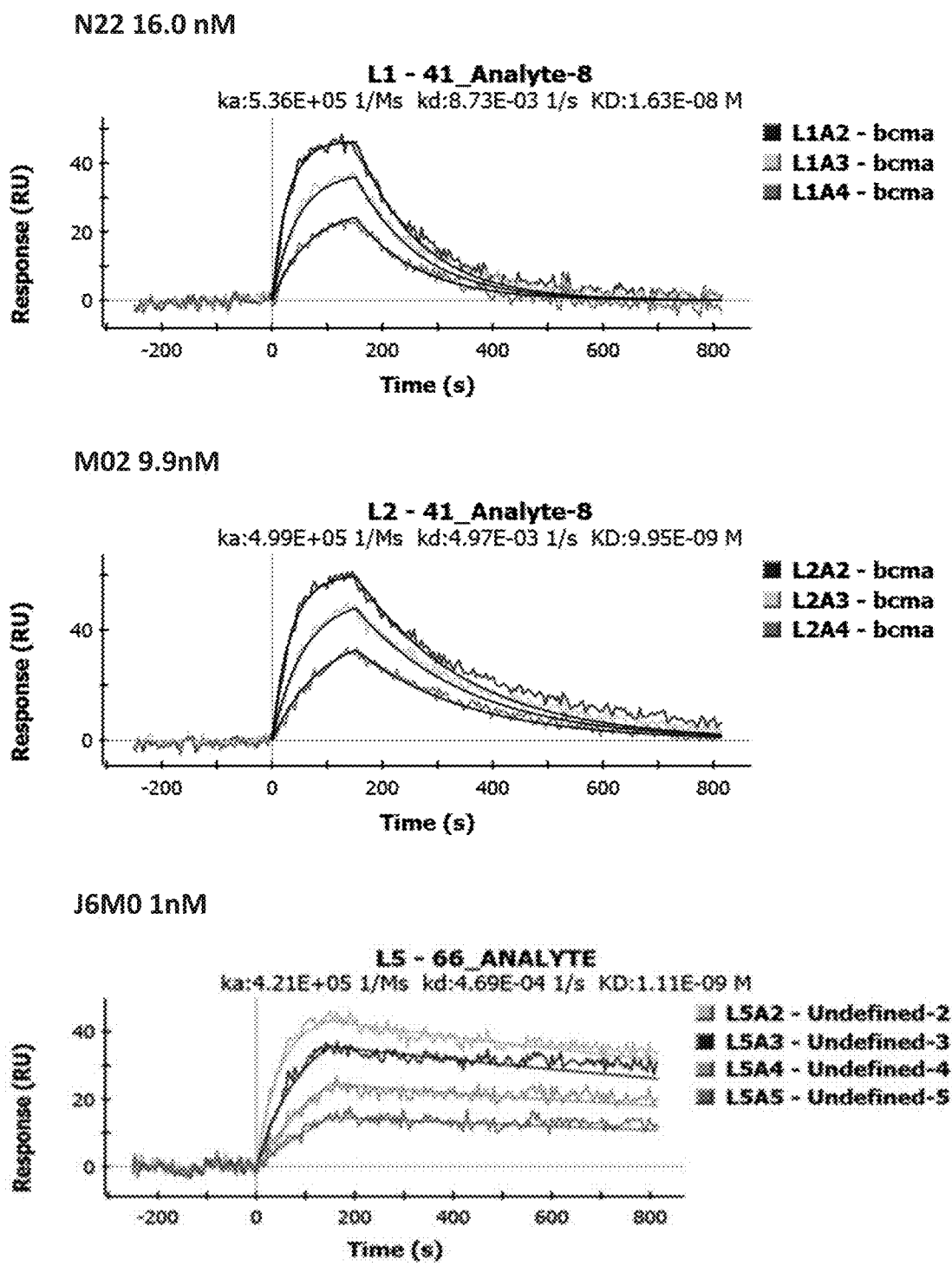

FIG. 14 are graphs illustrating the affinity and kinetics measurements of N22, M02, and J6M0 antibody binding to human BCMA using a SPR-based ProteOn™ system.

FIG. 15 are graphs illustrating the binding of 15B2GL, L15, 109, or J6M0 antibodies to NCI-H929, MM.1S, and Ad293+huBCMA cell lines measured by flow cytometry.

DETAILED DESCRIPTION OF THE INVENTION

The present disclosure provides an antibody-drug conjugate (ADC) comprising a monoclonal antibody, or an antigen-binding fragment thereof, directed against B-cell maturation antigen (BCMA) conjugated to a cytotoxin. The term "antibody-drug conjugate," as used herein, refers to a compound comprising a monoclonal antibody (mAb) attached to a cytotoxic agent (generally a small molecule drug with a high systemic toxicity) via chemical linkers. In some embodiments, an ADC may comprise a small molecule cytotoxin that has been chemically modified to contain a linker. The linker is then used to conjugate the cytotoxin to the antibody, or antigen-binding fragment thereof. Upon binding to the target antigen on the surface of a cell, the ADC is internalized and trafficked to the lysosome where the cytotoxin is released by either proteolysis of a cleavable linker (e.g., by cathepsin B found in the lysosome) or by proteolytic degradation of the antibody, if attached to the cytotoxin via a non-cleavable linker. The cytotoxin then translocates out of the lysosome and into the cytosol or nucleus, where it can then bind to its target, depending on its mechanism of action.

The term "monoclonal antibodies," as used herein, refers to antibodies that are produced by a single clone of B-cells and bind to the same epitope. In contrast, the term "polyclonal antibodies" refers to a population of antibodies that are produced by different B-cells and bind to different epitopes of the same antigen. The antibody-drug conjugate described herein may comprise a whole antibody or an antibody fragment. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have the same general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

The ADC may comprise an antigen-binding fragment of an antibody. The terms "antibody fragment," "antigen-binding fragment," "functional fragment of an antibody," and "antigen-binding portion" are used interchangeably herein and refer to one or more fragments or portions of an antibody that retain the ability to specifically bind to an antigen (see, generally, Holliger et al., *Nat. Biotech.*, 23(9): 1126-1129 (2005)). The antibody fragment may comprise, for example, one or more CDRs, the variable region (or portions thereof), the constant region (or portions thereof), or combinations thereof. Examples of antibody fragments include, but are not limited to, (i) a Fab fragment, which is a monovalent fragment consisting of the VL, VH, CL, and CH1 domains; (ii) a F(ab')2 fragment, which is a bivalent fragment comprising two Fab fragments linked by a disulfide bridge at the hinge region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., *Science,* 242: 423-426 (1988); Huston et al., *Proc. Natl. Acad. Sci. USA,* 85: 5879-5883 (1988); and Osbourn et al., *Nat. Biotechnol.,* 16: 778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Patent Application Publication 2009/0093024 A1.

In one embodiment, the antibody-drug conjugate described herein comprises a monoclonal antibody, or an antigen-binding fragment thereof, directed against B-cell Maturation Antigen (BCMA, also known as CD269). BCMA is a member of the tumor necrosis factor receptor superfamily (see, e.g., Thompson et al., *J. Exp. Medicine,* 192(1): 129-135 (2000), and Mackay et al., *Annu. Rev. Immunol.,* 21: 231-264 (2003)). BCMA binds B-cell activating factor (BAFF) and a proliferation inducing ligand (APRIL) (see, e.g., Mackay et al., supra, and Kalled et al, *Immunological Reviews,* 204: 43-54 (2005)). Among non-malignant cells, BCMA has been reported to be expressed mostly in plasma cells and subsets of mature B-cells (see, e.g., Laabi et al., *EMBO J.*, 77(11): 3897-3904 (1992); Laabi et al., *Nucleic Acids Res.*, 22(7): 1147-1154 (1994); Kalled et al., supra; O'Connor et al., *J. Exp. Medicine*, 199(1): 91-97 (2004); and Ng et al., *J. Immunol.*, 173(2): 807-817 (2004)). Mice deficient in BCMA are healthy and have normal numbers of B-cells, but the survival of long-lived plasma cells is impaired (see, e.g., O'Connor et al, supra; Xu et al., *Mol. Cell. Biol.*, 21(12): 4067-4074 (2001); and Schiemann et al., *Science*, 293(5537): 2111-2114 (2001)). BCMA RNA has been detected universally in multiple myeloma cells, and BCMA protein has been detected on the surface of plasma cells from multiple myeloma patients by several investigators (see, e.g., Novak et al, *Blood*, 103(2): 689-694 (2004); Neri et al., *Clinical Cancer Research*, 73(19): 5903-5909 (2007); Bellucci et al., *Blood*, 105(10): 3945-3950 (2005); and Moreaux et al., *Blood*, 703(8): 3148-3157 (2004)).

In some embodiments, the disclosure provides the monoclonal antibody, or an antigen-binding fragment thereof, directed against BCMA described above independent of an antibody-drug conjugate. The monoclonal antibody, or antigen-binding fragment thereof, may comprise (a) a heavy chain variable region comprising a complementarity determining region 1 (HCDR1) amino acid sequence of SEQ ID NO: 1, an HCDR2 amino acid sequence of SEQ ID NO: 2, and an HCDR3 amino acid sequence of SEQ ID NO: 3 and (b) a light chain variable region comprising a complementarity determining region 1 (LCDR1) amino acid sequence of SEQ ID NO: 4, an LCDR2 amino acid sequence of SEQ ID NO: 5, and an LCDR3 amino acid sequence of SEQ ID NO: 6. In another embodiment, the monoclonal antibody comprises a heavy chain variable region comprising the amino acid sequence of SEQ ID NO: 7 and/or a light chain variable region comprising the amino acid sequence of SEQ ID NO: 8.

The monoclonal antibody, or an antigen-binding fragment thereof, directed against BCMA may comprise any suitable binding affinity to BCMA or an epitope thereof. The term "affinity" refers to the equilibrium constant for the reversible binding of two agents and is expressed as the dissociation constant ($K_D$). The affinity of an antibody or antigen-binding fragment thereof for an antigen or epitope of interest can be measured using any method known in the art. Such methods include, for example, fluorescence activated cell sorting (FACS), surface plasmon resonance (e.g., Biacore™, ProteOn™), biolayer interferometry (BLI, e.g. Octet®), kinetics exclusion assay (e.g. KinExA™), separable beads (e.g., magnetic beads), antigen panning, and/or ELISA (see, e.g., Janeway et al. (eds.), *Immunobiology*, 5th ed., Garland Publishing, New York, N.Y., 2001). It is known in the art that the binding affinity of a particular antibody will vary depending on the method that is used to analyze the binding affinity.

A soluble form of BCMA (sBCMA) has been detected in the serum of multiple myeloma patients, with reported values ranging from 3.8 to 1062 ng/mL (Lee et al *Br J Haematol* 2016, Sanchez et al *Br J Haematol* 2012), and is comprised of the entire extracellular domain of the molecule (Laurent et. al. *Nat Commun* 2015). Therefore, sBCMA could diminish the effects of antibody-based therapies. The functional features of sBCMA and recombinant monomeric human BCMA are similar (Laurent et. al. *Nat Commun* 2015). Therefore, to mitigate the potential effects of sBCMA on the efficacy of a BCMA antibody-drug conjugate, it is desirable to select an antibody component that possesses weak binding to recombinant monomeric human BCMA and strong binding to membrane-bound BCMA.

Affinity of a binding agent to a ligand, such as affinity of an antibody for an epitope, can be, for example, from about 1 picomolar (pM) to about 1 micromolar (1 µM) (e.g., from about 1 picomolar (pM) to about 1 nanomolar (nM), or from about 1 nM to about 1 micromolar (µM)). In one embodiment, the monoclonal antibody or an antigen-binding fragment thereof may bind to BCMA with a $K_D$ less than or equal to 100 nanomolar (e.g., 100 nM, about 90 nM, about 80 nM, about 70 nM, about 60 nM, about 50 nM, about 40 nM, about 30 nM, about 20 nM, or about 10 nM, or a range defined by any two of the foregoing values). In another embodiment, the monoclonal antibody may bind to BCMA with a $K_D$ less than or equal to 10 nanomolar (e.g., about 9 nM, about 8.5 nM, about 8 nM, about 7.5 nM, about 7 nM, about 6.5 nM, about 6 nM, about 5.5 nM, about 5 nM, about 4.5 nM, about 4 nM, about 3.5 nM, about 3 nM, about 2.5 nM, about 2 nM, about 1.5 nM, about 1 nM, about 0.9 nM, about 0.8 nM, about 0.7 nM, about 0.6 nM, about 0.5 nM, about 0.4 nM, about 0.3 nM, about 0.2 nM, about 0.1 nM, about 0.05 nM, about 0.025 nM, about 0.01 nM, about 0.001 nM, or a range defined by any two of the foregoing values). In another embodiment, the monoclonal antibody may bind to BCMA with a $K_D$ less than or equal to 200 pM (e.g., about 190 pM, about 175 pM, about 150 pM, about 125 pM, about 110 pM, about 100 pM, about 90 pM, about 80 pM, about 75 pM, about 60 pM, about 50 pM, about 40 pM, about 30 pM, about 25 pM, about 20 pM, about 15 pM, about 10 pM, about 5 pM, about 1 pM, or a range defined by any two of the foregoing values).

In one embodiment, the affinity of the BCMA antibody or antigen-binding fragment thereof to monomeric BCMA, as measured by surface plasmon resonance (SPR), is about 90 nM, about 80 nM, about 70 nM, about 60 nM, about 50 nM, about 40 nM, about 30 nM, or a range defined by any two of the foregoing values, for example, about 50 nM to about 70 nM, about 55 nM to about 65 nM, or about 58 nM to about 62 nM.

In one embodiment, the affinity of the BCMA antibody or antigen-binding fragment thereof to membrane-bound BCMA, as measured by FACS, is less than or equal to 10 nanomolar (e.g., about 9 nM, about 8.5 nM, about 8 nM, about 7.5 nM, about 7 nM, about 6.5 nM, about 6 nM, about 5.5 nM, about 5 nM, about 4.5 nM, about 4 nM, about 3.5 nM, about 3 nM, about 2.5 nM, about 2 nM, about 1.5 nM, about 1 nM, about 0.9 nM, about 0.8 nM, about 0.7 nM, about 0.6 nM, about 0.5 nM, about 0.4 nM, about 0.3 nM, about 0.2 nM, about 0.1 nM, about 0.05 nM, about 0.025 nM, about 0.01 nM, about 0.001 nM, or a range defined by any two of the foregoing values).

An antigen-binding portion or fragment of a monoclonal antibody can be of any size so long as the portion binds to BCMA. In this respect, an antigen binding portion or fragment of the monoclonal antibody directed against BCMA (also referred to herein as an "anti-BCMA monoclonal antibody") desirably comprises between about 5 and 18 amino acids (e.g., about 5, 6, 7, 8, 9, 10, 11, 12, 13, 14, 15, 16, 17, 18, or a range defined by any two of the foregoing values).

In one embodiment, the antibody-drug conjugate comprises a variable region of an anti-BCMA monoclonal antibody. In this respect, the ADC may comprise a light chain variable region, a heavy chain variable region, or both a light chain variable region and a heavy chain variable region of an anti-BCMA monoclonal antibody. Preferably, the ADC comprises a light chain variable region and a heavy chain variable region of an anti-BCMA monoclonal antibody. Monoclonal antibodies that bind to BCMA are disclosed in, e.g., International Patent Application Publication WO 2010/104949. In one embodiment, the monoclonal antibody of the ADC described herein comprises (a) a heavy chain variable region comprising a complementarity determining region 1 (HCDR1) amino acid sequence of SYSMN (SEQ ID NO: 1), an HCDR2 amino acid sequence of SISGSSNYIYY-ADSVKG (SEQ ID NO: 2), and an HCDR3 amino acid sequence of GGNYYVEYFQY (SEQ ID NO: 3) and (b) a light chain variable region comprising a complementarity determining region 1 (LCDR1) amino acid sequence of RASQYISSNYLA (SEQ ID NO: 4), an LCDR2 amino acid sequence of GASNRAT (SEQ ID NO: 5), and an LCDR3 amino acid sequence of QQYGSSPIT (SEQ ID NO: 6). In another embodiment, the monoclonal antibody of the ADC described herein may comprise a heavy chain variable region comprising the amino acid sequence of SEQ ID NO: 7 and/or a light chain variable region comprising the amino acid sequence of SEQ ID NO: 8.

The terms "cytotoxin" and "cytotoxic agent" refer to any molecule that inhibits or prevents the function of cells and/or causes destruction of cells (cell death), and/or exerts antiproliferative effects. It will be appreciated that a cytotoxin or cytotoxic agent of an ADC also is referred to in the art as the "payload" of the ADC. A number of classes of cytotoxic agents are known in the art to have potential utility in ADC molecules and can be used in the ADC described herein. Such classes of cytotoxic agents include, for example, anti-microtubule agents (e.g., auristatins and maytansinoids), pyrrolobenzodiazepines (PBDs), RNA polymerase II inhibitors (e.g., amatoxins), and DNA alkylating agents (e.g., indolinobenzodiazepine pseudodimers). Examples of specific cytotoxic agents that may be used in the ADC described herein include, but are not limited to, amanitins, auristatins, calicheamicin, daunomycins, doxorubicins, duocarmycins, dolastatins, enediynes, lexitropsins, taxanes, puromycins, maytansinoids, *vinca* alkaloids, tubulysins, and pyrrolobenzodiazepines (PBDs). More specifically, the cytotoxic agent may be, for example AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM1, DM4, vinblastine, methotrexate, netropsin, or derivatives or analogs thereof. Cytotoxins suitable for use in ADCs are also described in, for example, International Patent Application Publication Nos. WO 2015/155345 and WO 2015/157592.

In one embodiment, the cytotoxic agent may be an anti-microtubule agent, such as a tubulysin, a maytansinoid, an auristatin, or derivatives thereof. The terms "anti-microtubule agent" and "microtubule-targeting agent," are synonymous and refer to an agent that inhibits cell division by interfering with microtubules. Tubulysins are members of a class of natural products isolated from myxobacterial species (Sasse et al., *J. Antibiot.*, 53: 879-885 (2000)), which act as mitotic poisons that inhibit tubulin polymerization and lead to cell cycle arrest and apoptosis (Steinmetz et al., *Chem. Int. Ed.*, 43: 4888-4892 (2004); Khalil et al., *Chem. Biochem.*, 7: 678-683 (2006); Kaur et al., *Biochem. J.*, 396: 235-242 (2006)). Examples of tubulysins are disclosed in, for example, International Patent Application Publication Nos. WO 2015/157594, WO 2004/005326, WO 2012/019123, WO 2009/134279, WO 2009/055562, WO 2004/005327; U.S. Pat. Nos. 7,776,841, 7,754,885, and 7,816,377; and U.S. Patent Application Publications 2010/0240701, 2011/0021568, and 2011/0263650.

In certain aspects, the tubulysin is a compound described in WO 2015/157594, which is incorporated by reference herein, such as, for example, a compound having the following structure:

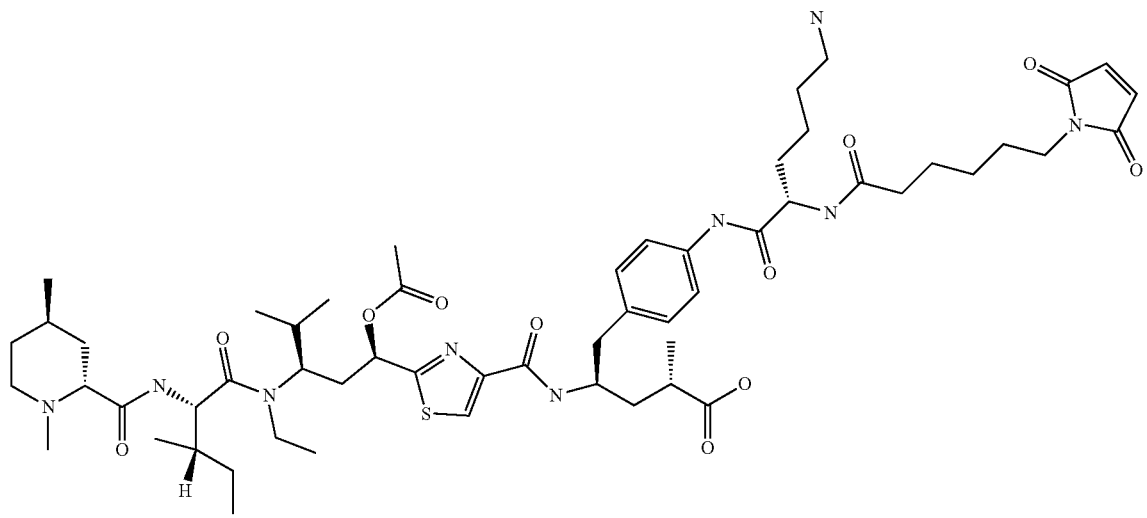

Or a compound having the following structure:

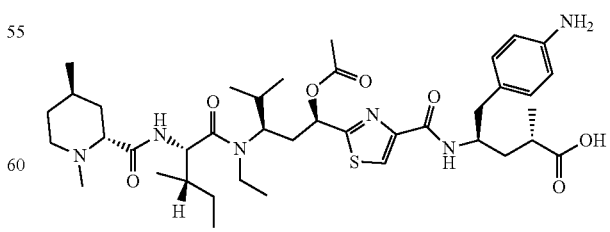

Maytansinoids inhibit polymerization of the microtubule protein tubulin, thereby preventing formation of microtubules (see, e.g., U.S. Pat. No. 6,441,163 and Remillard et al., Science, 189: 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208,020). Maytansinoids include maytansine, maytansinol, C-3 esters of maytansinol, and other maytansinol analogues and derivatives (see, e.g., U.S. Pat. Nos. 5,208,020 and 6,441,163). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues also are known in the art and described in, for example, Kupchan et al., *J. Med. Chem.*, 21: 31-37 (1978). Methods for generating maytansinol and analogues and derivatives thereof are described in, for example, U.S. Pat. No. 4,151,042. Examples of maytansinoids that may be used in connection with the ADC described herein include, but are not limited to, N2'-deacetyl-N2'-(3-mercapto-1-oxopropyl)-maytansine (DM1) and N2'-deacetyl-N2'-(4-mercapto-4-methyl-1-oxopentyl)-maytansine (DM4).

Auristatins represent a class of highly potent antimitotic agents that have shown substantial preclinical activity at well-tolerated doses (Law et al., *Cancer Res.*, 66: 2328-2337 (2006); Ma et al., *Clin. Cancer Res.*, 12: 2591-2596 (2006); Tse et al., *Cancer Res.*, 12: 1373-1382 (2006); and Oflazoglu et al., *Br. J. Haematol.*, 142: 69-73 (2008), and Oflazoglu et al., *Clin. Cancer Res.*, 14: 6171-6180 (2008)). Auristatin ADCs are currently being evaluated in preclinical and clinical trials. Examples of auristatins that may be used in connection with the ADC described herein include, but are not limited to, monomethyl auristatin E (MMAE) and the related molecule monomethyl auristatin F (MMAF) (see, e.g., Doronina et al., *Nat. Biotechnol.*, 21: 778-784 (2003); and Doronina et al., *Bioconjug. Chem.*, 17: 114-124 (2006)).

In one embodiment, the cytotoxic agent may be a pyrrolobenzodiazepine (PBD) or a PBD derivative. PBD translocates to the nucleus where it crosslinks DNA, preventing replication during mitosis, damaging DNA by inducing single strand breaks, and subsequently leading to apoptosis. Some PBDs also have the ability to recognize and bind to specific sequences of DNA. PBDs are of the general structure:

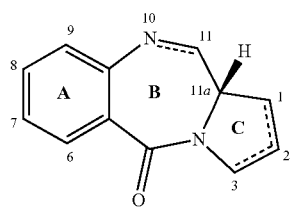

PBDs differ in the number, type, and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position, which is the electrophilic centre responsible for alkylating DNA. All of the known natural products have an (S)-configuration at the chiral C11a position which provides them with a right-handed twist when viewed from the C ring towards the A ring. This feature also gives PBDs the appropriate three-dimensional shape for isohelicity with the minor groove of B-form DNA, leading to a snug fit at the binding site (Kohn, In: *Antibiotics III.* Springer-Verlag, New York, pp. 3-11 (1975); and Hurley and Needham-VanDevanter, *Acc. Chem. Res.*, 19: 230-237 (1986)). PBDs can form adducts in the minor groove, leading to interference with DNA processing.

The first PBD anti-tumor antibiotic, anthramycin, was discovered in 1965 (Leimgruber et al., *J. Am. Chem. Soc.*, 87: 5793-5795 (1965); Leimgruber et al., *J. Am. Chem. Soc.*, 87: 5791-5793 (1965)). Since then, a number of naturally occurring PBDs have been reported, and over ten synthetic routes have been developed for a variety of analogues (Thurston et al., *Chem. Rev.*, 433-465 (1994); and Antonow, D. and Thurston, D. E., *Chem. Rev.*, 111: 2815-2864 (2011)). Family members include abbeymycin (Hochlowski et al., *J. Antibiotics*, 40: 145-148 (1987)), chicamycin (Konishi et al., *J. Antibiotics*, 37: 200-206 (1984)), DC-81 (Japanese Patent 58180487; Thurston et al., *Chem. Brit.*, 26: 767-772 (1990); and Bose et al., *Tetrahedron*, 48: 751-758 (1992)), mazethramycin (Kuminoto et al., *J. Antibiotics*, 33: 665-667 (1980)), neothramycins A and B (Takeuchi et al., *J. Antibiotics*, 29: 93-96 (1976)), porothramycin (Tsunakawa et al., *J. Antibiotics*, 41: 1366-1373 (1988)), prothracarcin (Shimizu et al., *J. Antibiotics*, 29: 2492-2503 (1982); and *Langley and Thurston, J. Org. Chem.*, 52: 91-97 (1987)), sibanomicin (DC-102) (Hara et al., *J. Antibiotics*, 41: 702-704 (1988); and Itoh et al., *J. Antibiotics*, 41: 1281-1284 (1988)), sibiromycin (Leber et al., *J. Am. Chem. Soc.*, 110: 2992-2993 (1988)) and tomamycin (Arima et al., *J. Antibiotics*, 25: 437-444 (1972)). PBDs, as well as ADCs comprising PBDs, also are described in International Patent Application Publication Nos. WO 2015/155345 and WO 2015/157592.

In one embodiment, the PBD is PBD 3249, also referred to herein as "SG3249" and described in detail in WO 2014/057074, which has the following structure:

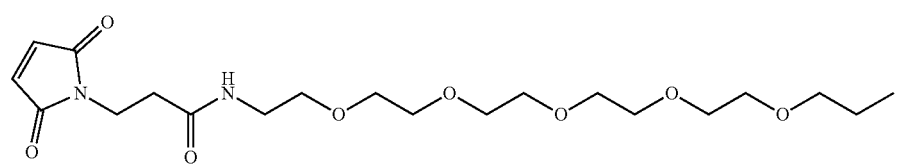

-continued
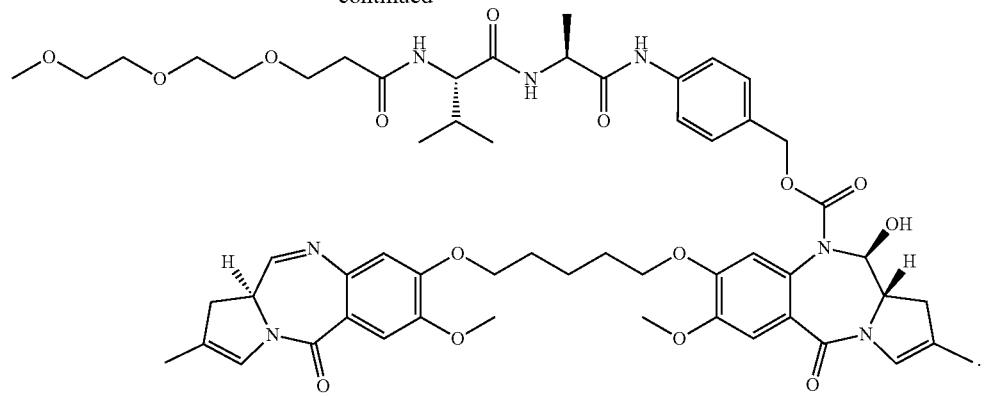
In another embodiment, the PBD is PBD 3315, also referred to herein as "SG3315" and described in detail in WO 2015/052322, which has the following structure:
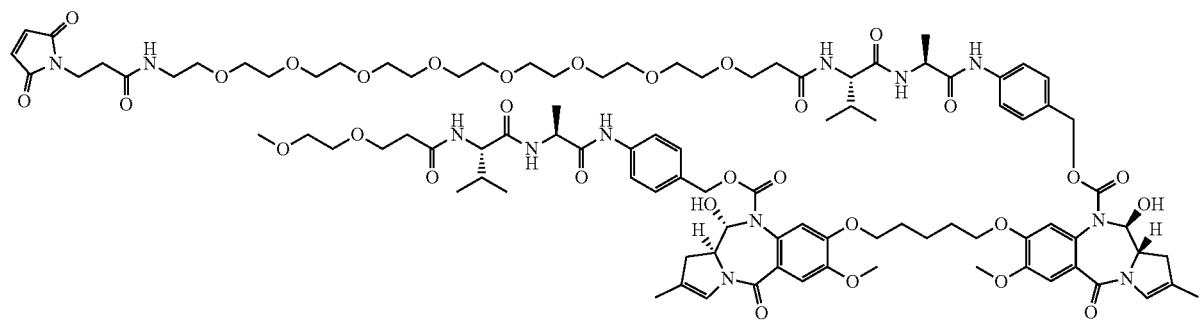 [SMILES: COCCOCCC(=O)N[C@H](C(=O)N[C@@H](C)C(=O)Nc1ccc(COC(=O)N2c3cc(OCCCCCOc4cc5c(cc4OC)C(=O)N4C=C(C)C[C@H]4[C@H](O)N5C(=O)OCc4ccc(NC(=O)[C@H](C)NC(=O)[C@@H](NC(=O)CCOCCOCCOCCOCCOCCOCCOCCOCCNC(=O)CCN5C(=O)C=CC5=O)C(C)C)cc4)c(OC)cc3C(=O)N3C=C(C)C[C@H]3[C@@H]2O)cc1)C(C)C]
In another embodiment, the PBD is SG3400, also referred to as Compound 23, which is described in detail in PCT/EP2017/052988, filed on 10 Feb. 2017, and has the following structure:
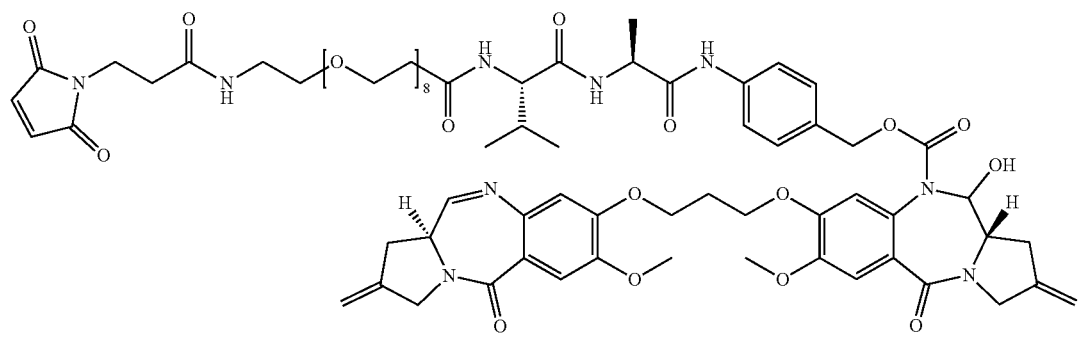

The BCMA monoclonal antibody, or antigen-binding fragment thereof, may be conjugated to a cytotoxin using any suitable method known in the art, including site-specific or non-site specific conjugation methods. Conventional conjugation strategies for antibodies typically rely on randomly (i.e., non-specifically) conjugating the payload to the antibody, antigen-binding fragment thereof, through lysines or cysteines. Accordingly, in some aspects the antibody or antigen-binding fragment thereof is randomly conjugated to a cytotoxic agent, for example, by partial reduction of the antibody or antibody fragment, followed by reaction with a desired agent with or without a linker moiety attached. For example, the antibody or antigen-binding fragment thereof may be reduced using dithiothreitol (DTT) or a similar reducing agent. The cytotoxic agent, with or without a linker moiety attached thereto, can then be added at a molar excess to the reduced antibody or antibody fragment in the presence of dimethyl sulfoxide (DMSO). After conjugation, excess free cysteine may be added to quench unreacted agent. The reaction mixture may then be purified and buffer-exchanged into phosphate buffered saline (PBS).

In other embodiments, the cytotoxic agent may be conjugated to the BCMA monoclonal antibody using site-specific conjugation methods at specific reactive amino acid residues, yielding homogeneous ADC preparations with uniform stoichiometry. Site-specific conjugation may be through a cysteine residue or a non-natural amino acid. In one embodiment, the cytotoxic agent may be conjugated to the antibody, or antigen binding fragment thereof, through at least one cysteine residue. In particular, for example, a cytotoxic agent may be chemically conjugated to the side chain of an amino acid at a specific Kabat position in the Fc region of the BCMA monoclonal antibody. In this regard, the cytotoxic agent may be conjugated to the BCMA monoclonal antibody through a cysteine residue at any suitable position in the Fc region of the antibody, including but not limited to, a cysteine at least one of positions 239, 248, 254, 273, 279, 282, 284, 286, 287, 289, 297, 298, 312, 324, 326, 330, 335, 337, 339, 350, 355, 356, 359, 360, 361, 375, 383, 384, 389, 398, 400, 413, 415, 418, 422, 440, 441, 442, 443 and 446, wherein the numbering corresponds to the EU index in Kabat. In one embodiment, the cytotoxic agent may be conjugated to the BCMA monoclonal antibody through a cysteine residue at the specific Kabat positions 239 and/or 442 of the BCMA monoclonal antibody, and/or through an amino acid residue inserted between Kabat positions 239 and 240 of the BCMA antibody (Dimasi et al., *Mol Pharm*, 14(5):1501-1516 (2017). Alternatively, the cytotoxic agent may be conjugated to the BCMA monoclonal antibody or antigen binding fragment thereof through a thiol-maleimide linkage, such as, for example, via a sulfhydryl reactive group at the hinge and heavy-light chains.

The BCMA monoclonal antibody described herein comprises at least one cytotoxin molecule conjugated thereto; however, the BCMA monoclonal antibody may comprise any suitable number of cytotoxin molecules conjugated thereto (e.g., 1, 2, 3, 4, or more cytotoxin molecules) to achieve a desired therapeutic effect. Desirably, the ADC described herein comprises two cytotoxin molecules conjugated to a BCMA monoclonal antibody.

The BCMA antibody described herein is useful for any therapeutic in which it is desirable to target BCMA, such as adoptive cell transfer (ACT), bispecific T-cell engagers (BiTEs), and nanoparticles. In one embodiment, the disclosure provides a chimeric antigen receptor (CAR) comprising an antigen binding domain of the BCMA monoclonal antibody described herein linked to a T-cell activation moiety. A "chimeric antigen receptor (CAR)" is an artificially constructed hybrid protein or polypeptide containing an antigen binding domain of an antibody (e.g., a single chain variable fragment (scFv)) linked to T-cell signaling or T-cell activation moeities. CAR structures have evolved over the last twenty years to most commonly incorporate a single chain variable fragment (scFv) derived from a monoclonal antibody (mAb) and the signaling motif from the TCR chain (referred to as a "first-generation" CAR (see, e.g., Okur, F. V., Brenner, M. K., *Methods Mol. Biol.,* 651: 319-45 (2010); and Lee et al., *Clin. Cancer. Res.,* 18(10): 2780-2790 (2012)). More recently, second and third generation CARs have been developed, which incorporate one ("second generation") or two ("third generation") costimulatory activating motifs from, for example, CD28, 4-1BB (CD137), and/or CD134 (OX-40), which enhance proliferation, cytotoxicity, and persistence in vivo (see, e.g., Finney et al., *J. Immunol.,* 172: 104-13 (2004); Imai et al., *Leukemia,* 18: 676-84 (2004); Maher et al., *Nat Biotechnol.,* 20:70-5 (2002); Milone et al., *Mol Ther.,* 17: 1453-64 (2009); and Lee et al., supra).

The antigen binding domain of the CAR may comprise a whole monoclonal antibody or a monoclonal antibody fragment, as described herein. In one embodiment, the antigen binding domain of the CAR may comprise a single chain Fv (scFv) fragment of the anti-BCMA monoclonal antibody. Chimeric antigen receptors and methods for generating CARs are further described in, for example, Riviere, I. and M. Sadelain, *Mol. Ther.,* 25(5): 1117-1124 (2017); Davila, M. L. and M. Sadelain, *Int. J. Hematol.,* 104(1): 6-17 (2016); and U.S. Patent Application Publication 2015/0051266 A1.

The disclosure also provides a composition comprising the above-described antibody or antibody-drug conjugate and a pharmaceutically acceptable (e.g., physiologically acceptable) carrier. Any suitable carrier known in the art can be used within the context of the invention. The choice of carrier will be determined, in part, by the particular site to which the composition may be administered and the particular method used to administer the composition. The composition optionally may be sterile. The compositions can be generated in accordance with conventional techniques described in, e.g., *Remington: The Science and Practice of Pharmacy,* 21st Edition, Lippincott Williams & Wilkins, Philadelphia, Pa. (2001).

The composition desirably comprises the antibody or antibody-drug conjugate in an amount that is effective to treat or prevent multiple myeloma. Thus, the disclosure provides a method of killing multiple myeloma cells, which comprises contacting multiple myeloma cells that express BCMA with the antibody or antibody-drug conjugate described herein, or a composition comprising the antibody or ADC described herein, whereby the antibody or antibody-drug conjugate binds to BCMA on the multiple myeloma cells and kills the multiple myeloma cells. The disclosure also provides use of the antibody or ADC described herein, or the composition comprising the antibody or ADC, in the manufacture of a medicament for treating multiple myeloma. As discussed herein, multiple myeloma, also known as plasma cell myeloma or Kahler's disease, is a cancer of plasma cells, which are a type of white blood cell normally responsible for the production of antibodies (Raab et al., *Lancet,* 374: 324-329 (2009)). Multiple myeloma affects 1-4 per 100,000 people per year. The disease is more common in men, and for yet unknown reasons is twice as common in African Americans as it is in Caucasian Americans. Multiple myeloma is the least common hematological malignancy (14%) and constitutes 1% of all cancers (Raab et al., supra). Treatment of multiple myeloma typically involves high-dose chemotherapy followed by hematopoietic stem cell transplantation (allogenic or autologous); however, a high rate of relapse is common in multiple myeloma patients that have undergone such treatment. As discussed above, BCMA is highly expressed by multiple myeloma cells (see, e.g., Novak et al., supra; Neri et al., supra; Bellucci et al., supra; and Moreaux et al., supra).

As demonstrated herein, BCMA also is expressed on multiple myeloma stem cells. As such, the disclosure provides a method of killing multiple myeloma stem cells, which comprises contacting multiple myeloma stem cells that express BCMA with the antibody-drug conjugate described herein, or a composition comprising the ADC described herein, whereby the antibody-drug conjugate binds to BCMA on the multiple myeloma stem cells and kills the multiple myeloma stem cells. Multiple myeloma stem cells can be identified in the bone marrow of multiple myeloma patients by their surface expression of CD19 and lack of CD138 surface expression (see, e.g., Matsui et al., *Blood,* 103: 2332-6 (2004)). These cells are uniquely clonogenic and engraft immunodeficient mice, whereas the myeloma plasma cells, defined as CD138+CD19−, do not. Multiple myeloma stem cells also are resistant to current therapies (Matsui et al., *Cancer Res.,* 68: 190-7 (2008)).

The antibody-drug conjugate described herein, or a composition comprising the antibody-drug conjugate, may be contacted with a population of multiple myeloma cells that expresses BCMA ex vivo, in vivo, or in vitro. "Ex vivo" refers to methods conducted within or on cells or tissue in an artificial environment outside an organism with minimum alteration of natural conditions. In contrast, the term "in vivo" refers to a method that is conducted within living organisms in their normal, intact state, while an "in vitro" method is conducted using components of an organism that have been isolated from their usual biological context. In one embodiment, the multiple myeloma cells are human multiple myeloma cells that are contacted with the ADC described herein, or a composition comprising the ADC, in vivo.

As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the antibody or ADC or the composition comprising the antibody or ADC and a pharmaceutically acceptable carrier. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the antibody or ADC to elicit a desired response in the individual. For example, a therapeutically effective amount of the ADC of the invention is an amount which binds to BCMA on multiple myeloma cells and destroys them.

Alternatively, the pharmacologic and/or physiologic effect may be prophylactic, i.e., the effect completely or partially prevents a disease or symptom thereof. In this respect, the inventive method comprises administering a "prophylactically effective amount" of the ADC or a composition comprising the ADC to a mammal that is predisposed to multiple myeloma. A "prophylactically effective amount" refers to an amount effective, at dosages and for periods of time necessary, to achieve a desired prophylactic result (e.g., prevention of disease onset).

Therapeutic or prophylactic efficacy can be monitored by periodic assessment of treated patients. In one embodiment, the ADC described herein inhibits or suppresses proliferation of BCMA-expressing myeloma cells by at least about 10% (e.g., at least about 20%, at least about 30%, at least about 40%, at least about 50%, at least about 60%, at least about 70%, at least about 80%, at least about 90%, or at least about 100%). Cell proliferation can be measured using any suitable method known in the art, such as measuring incorporation of labeled nucleosides (e.g., 3H-thymidine or bromodeoxyuridine Brd(U)) into genomic DNA (see, e.g., Madhavan, H. N., *J. Stem Cells Regen. Med.,* 3(1): 12-14 (2007)).

The antibody or ADC described herein, or a composition comprising the antibody ADC, can be administered to a mammal (e.g., a human) using standard administration techniques, including, for example, intravenous, intraperitoneal, subcutaneous. More preferably, the antibody or ADC or composition containing the same is administered to a mammal by intravenous injection.

The antibody or ADC described herein, or the composition comprising the antibody or ADC, can be administered with one or more additional therapeutic agents, which can be coadministered to the mammal. The term "coadministering," as used herein, refers to administering one or more additional therapeutic agents and the antibody or ADC described herein, or the antibody or ADC-containing composition, sufficiently close in time such that the antibody or ADC can enhance the effect of one or more additional therapeutic agents, or vice versa. In this regard, the antibody or ADC or the composition containing the same may be administered first, and the one or more additional therapeutic agents may be administered second, or vice versa. For example, the antibody or ADC or composition containing the same may be administered in combination with other agents (e.g., as an adjuvant) for the treatment or prevention of multiple myeloma. In this respect, the antibody or ADC or antibody or ADC-containing composition can be used in combination with at least one other anticancer agent including, for example, any suitable chemotherapeutic agent known in the art, ionization radiation, small molecule anticancer agents, cancer vaccines, biological therapies (e.g., other monoclonal antibodies, cancer-killing viruses, gene therapy, and adoptive T-cell transfer), and/or surgery.

The following examples further illustrate the invention but, of course, should not be construed as in any way limiting its scope.

Example 1

This example describes the generation of a monoclonal antibody directed against B-cell maturation antigen (BCMA).

Following the RIMMS immunization regime described in Kilpatrick et al., *Hybridoma,* 16(4): 381-389 (1997), six week old female Ablexis transgenic mice (Ablexis, LLC, San Francisco, Calif.) received six rounds of subcutaneous injections of purified recombinant human (rHu) BCMA-Fc alone (campaign 1), or alternating immunization with both rHu BCMA-Fc and cynomolgus BCMA-Fc (Cyno BCMA-Fc) or adherent 293 cells (Ad293) expressing either Hu BCMA or Cyno BCMA (campaign 2) at multiple sites. Mice were immunized over a course of 13 days at intervals of 2-3 days. For each round of immunization, mice were first anesthetized with isoflurane. The immunogen was emulsified in complete or incomplete Freund's adjuvant and TITERMAX® Gold adjuvant (Sigma-Aldrich, St. Louis, Mo.) and injected bilaterally at multiple sites. Test bleeds were collected on day 13 and assayed in antigen ELISA and FACS binding on adherent 293 cells expressing human and cynomolgus BCMA. Mice with good serum titers were given a pre-fusion boost intraperitoneally and sacrificed on day 17. Lymph node cells were harvested and fused to myeloma cell line P3-X63-Ag8.653 following the polyethylene glycol fusion method (Roche Diagnostics, Indianapolis, Ind.) to generate stable hybridomas.

Anti-BCMA-specific hybridomas were identified by screening the hybridoma supernatants in direct binding ELISA followed by FACS on BCMA-expressing Ad293 cells. Positive hybridomas were further tested for their ability to bind, internalize, and kill NCI-H929 multiple myeloma cells in vitro using a secondary-saporin conjugate, Fab-ZAP (Advanced Targeting Systems, San Diego, Calif., IT-48) and by FACS binding to endogenous BCMA expressed on cell lines. Based on internalization and cell killing potency, hybridomas were then limited dilution cloned and expanded for antibody purification and variable region gene rescue.

The first campaign yielded a panel of 44 human-only binders, and 4 human and cynomolgus cross-reactive binders. These 48 antibodies were then further tested by FACS on BCMA-expressing adherent 293 cells and endogenous huBCMA-expressing NCI-H929 cell lines. A lead panel of 25 hybridoma lines was identified by ranking the antibodies by best binding to endogenous human BCMA. A total of 11 hybridomas were advanced to subcloning, scale-up, sequencing, and purification. The clones also were evaluated for Fab-ZAP based killing. One antibody (clone 4679) was recombinantly cloned as a human IgG1 for further evaluation.

The second campaign yielded a panel of 98 binders for the immunization with rHu/Cyno BCMA-Fc, nine binders for the immunization with rHu/Cyno BCMA-Fc and Cyno BCMA-expressing Ad293 cells, and zero binders for the immunization with Ad293 cells expressing both Hu and Cyno BCMA. These hybridomas were further tested for binding to TACI and BAFF-R by FACS, and antibodies showing any detectable binding to TACI and BAFF-R were eliminated. These secondary screens along with the Fab-ZAP assay resulted in the identification of eight hybridomas that were moved forward for limited dilution cloning (LDC). Based on their activity, two clones (clones 756 and 15B2) were then converted into human IgG1 for further evaluation.

Figure 1A:
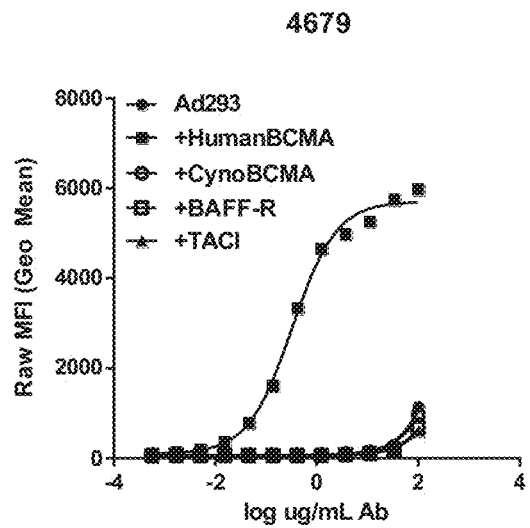
FIG. 1 is a series of graphs (FIG. 1A-1C) illustrating FACS binding of purified antibodies to adherent 293 (Ad293) cells expressing huBCMA, cynoBCMA, BAFF-R, and TACI as described in Example 1. The 15B2GL monoclonal antibody was the only cynomolgus cross-reactive antibody tested that did not bind to BAFF-R and/or TACI.
Figure 1B:
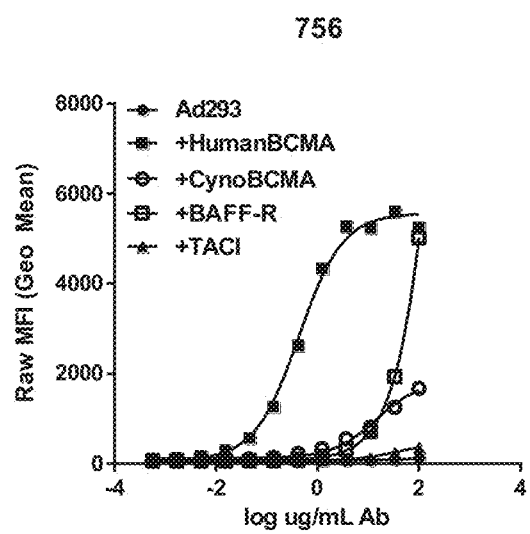
Figure 1C:
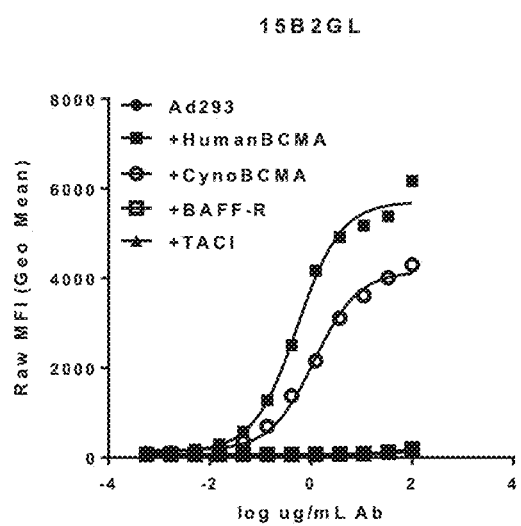
Figure 2A:
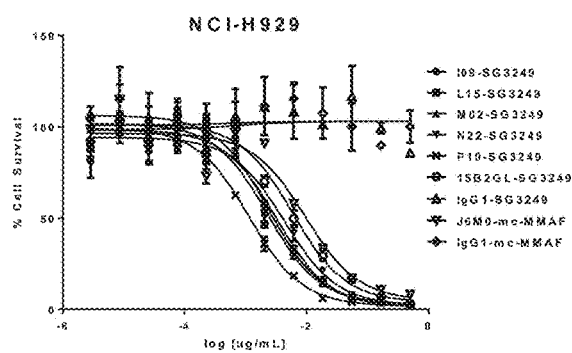
Figure 2B:
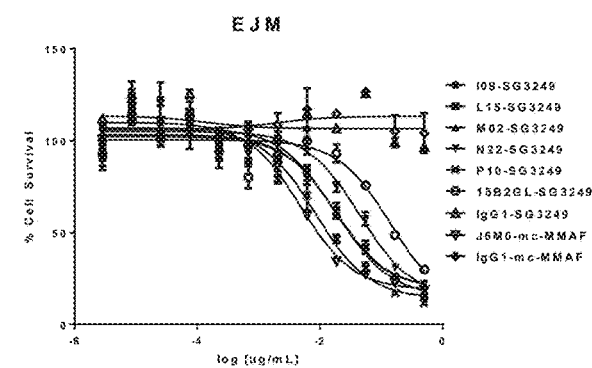
Figure 2C:
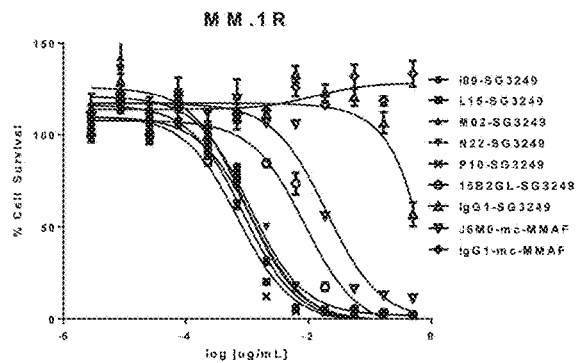
Figure 2D:
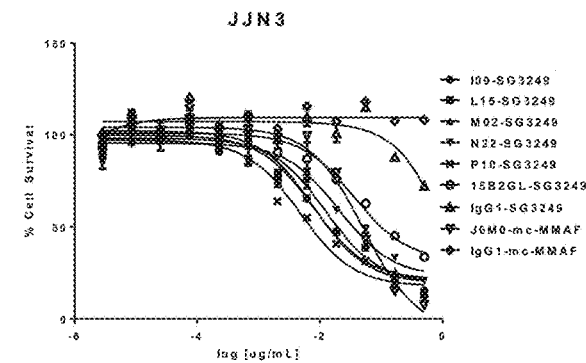
Figure 2E:
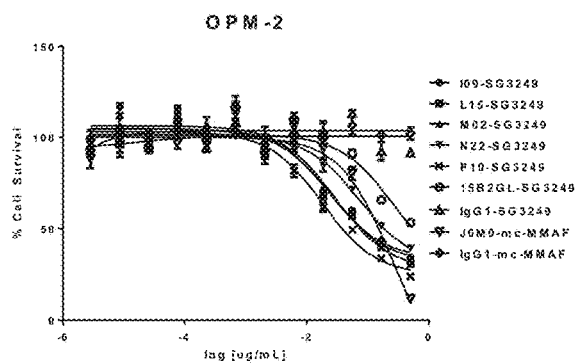
Figure 2F:
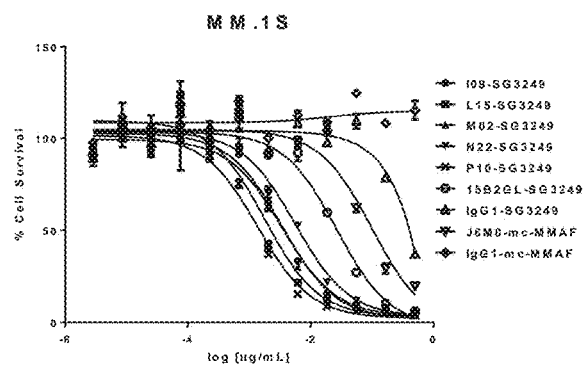
Figure 2G:
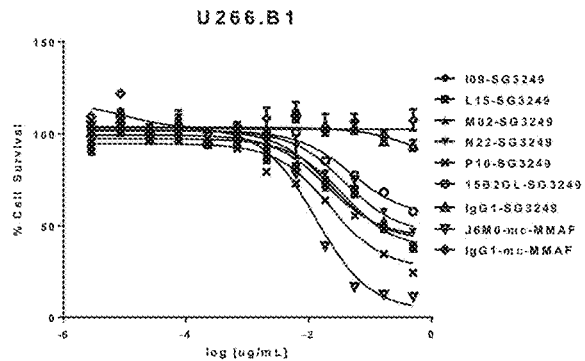
Figure 2H:
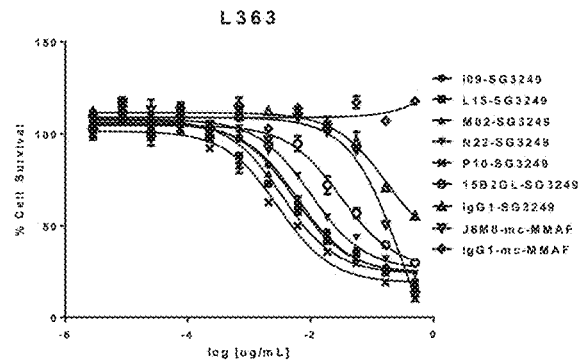
Figure 2I:
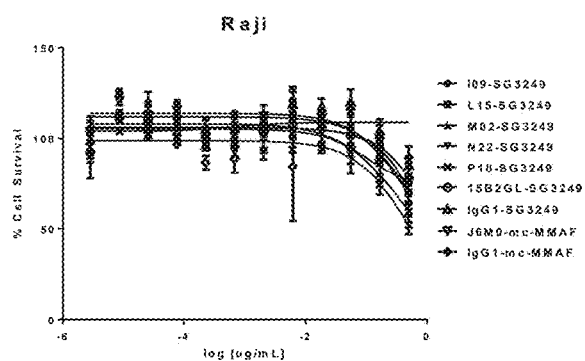
Figure 2J:
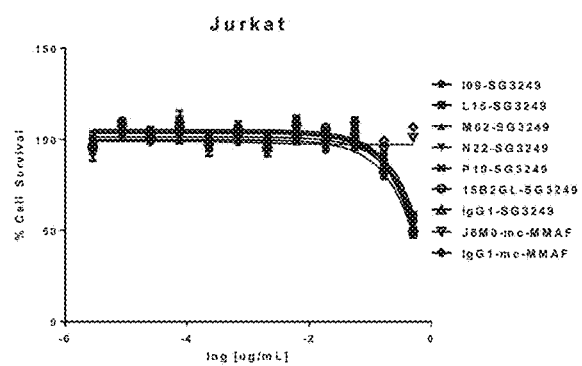

Antibodies 4679, 756, and 15B2GL (as described below) were analyzed by FACS to evaluate binding of antibodies to human BCMA, cynomolgus monkey BCMA, TACI, and BAFF-R using recombinant forms of the receptors stably expressed on Ad293 cells. Binding assays were performed by incubating antibodies 4679, 756, and 15B2GL with 200,000 cells at 4° C. for 45 minutes followed by two washes with PBS+2% FBS. Cells were then incubated with Alexa-Fluor® 647-labeled secondary antibodies at 4° C., followed by two washes in PBS+2% FBS. Anti-BAFF-R, anti-TACI, and anti-human BCMA-APC labeled antibodies were added according to manufacturer's recommended dilution in control wells. Cells were resuspended in 200 uL PBS+2% FBS+DAPI and antibody binding to live cells was analyzed using a Becton Dickinson™ Biosciences LSRII cytometer. Antibody 15B2GL was the only cyno-cross reactive antibody tested that did not bind to BAFF-R and/or TACI, as shown in FIG. 1.

The 15B2 monoclonal antibody was mutated to a germline form (15B2GL) using primers designed to mutate four non-germlined residues in 15B2. 15B2 wild-type DNA was used as template DNA for QuikChange Lightning mutagenesis (Agilent Genomics, Santa Clara, Calif.). STBIII cells (Invitrogen/Thermofisher Scientific, Waltham, Mass.) were used for transformation. After sequence verification, BCMA binding and kinetic assays were performed to compare the binding of 15B2GL and 15B2WT, and a collection of lead optimized (LO) clones of 15B2GL were generated. Briefly, 15B2 was cloned into a FAb expression vector designed for bacterial expression. Twenty seven residues in the heavy chain and nineteen residues in the light chain were each parsimoniously mutated with primers designed to allow for nineteen different amino acids excluding cysteine. Mutagenesis was performed using the QuikChange Lightning Mutagenesis kit (Agilent Genomics, Santa Clara, Calif.).

Approximately one hundred colonies per position were screened by binding ELISA, for a total of 6000 clones. ELISA binding was measured by capturing a low density of human BCMA and using bacterial supernatant after 48 hours of bacterial expression. Hits were defined as greater than two fold above 15B2GL control. Individual amino acid hits were confirmed by ELISA to cynomolgus BCMA with no binding to nonspecific protein. Identified hits from the parsimonious screen were then combined for primer design to generate a combinatorial library. The above FAb screening approach with ELISA binding was repeated as a combinatorial library using 15B2GL as the parental template and ELISA control. Hits identified after combinatorial screening were then cloned into an IgG mammalian expression vector ("Maia") designed for ADC conjugation. Proteins were expressed in 293HEK cells and purified by protein A affinity chromatography for further testing.

The ability of the 15B2GL antibody and LO clones of 15B2GL to bind, internalize, and kill H929 multiple myeloma cells in vitro was assessed using Fab-ZAP and by FACS binding to endogenous BCMA expressed on cell lines as described above. Briefly, antibodies were incubated with 200,000 cells for 30 minutes at 4° C. followed by two washes with PBS+2% FBS. Cells were resuspended in 100 uL cold PBS+2% FBS and kept at 4° C. At certain timepoints, cells were washed and resuspended in warm RPMI+ 10% FBS and placed into a 37° C. incubator, 5% $CO_2$. At the end of the experiment, cells were washed and then incubated with Alexa-Fluor® 647-labeled secondary antibodies at 4° C., followed by two washes in PBS+2% FBS. Cells were resuspended in 200 μL PBS+2% FBS+DAPI and antibody binding to live cells was analyzed using a Becton Dickinson Biosciences LSRII cytometer. The 15B2GL antibody exhibited unique and rapid internalization by this method as compared to the anti-BCMA antibody J6M0 (described in U.S. Pat. No. 9,273,141) and the LO antibodies.

Based on BCMA binding, kinetic screens (discussed above), and internalization, monoclonal antibody 15B2GL was selected, and five LO clones (i.e., I09, L15, P10, N22, and M02) were chosen for purification and conjugation along with 15B2GL.

The amino acids sequences of the heavy and light chain variable regions of the monoclonal antibodies 15B2 (wild-type and germlined) and LO clones I09, L15, P10, N22, and M02 are shown in Table 1.

TABLE 1

| Antibody | Amino Acid Sequence | SEQ ID NO: |
|---|---|---|
| 15B2GL VH | EVQLVESGGGLVKPGGSLRLSCAASGFTFRSYSMNW VRQAPGKGLEWVSSISGSSNYIYYADSVKGRFTISRD NAKNSLYLQMNSLRAEDTAVYYCARGGNYYVEYFQ YWGQGTLVTVSS | 7 |
| 15B2GL VL | EIVLTQSPGTLSLSPGERATLSCRASQYISSNYLAWYQ QKPGQAPRLLIYGASNRATGIPDRFSGSGSGTDFTLTI SRLEPEDFAVYYCQQYGSSPITFGQGTKLEIK | 8 |
| 15B2WT Variable Heavy Chain (VH) | EIQLVESGGGLVKPGGSLRLSCAASGFTFRSYSMNW VRQAPGKGLEWVSSISGSSNYIYYADSVKGRFTISRD NAKNSLYLQMNSLRAEDTALYYCARGGNYYVEYFQ YWGQGTLVTVSS | 9 |
| 15B2WT Variable Light Chain (VL) | EIVLTQSPGTLSLSPGERATLSCRASQYISSNYLAWYQ QKPGQAPRLLIYGASNRATGIPDRFSGSGSGTGFTLTI SRLEPEDFAVFYCQQYGSSPITFGQGTKLEIK | 10 |
| I09 VH | EVQLVESGGGLVKPGGSLRLSCAASGFTFSSYSMNW VRQAPGKGLEWVSSISGSSNYIYYADSVKGRFTISRD NAKNSLYLQMNSLRAEDTAVYYCARGGNYFVEYFQ QWGQGTLVTVSS | 11 |
| I09 VL | EIVLTQSPGTLSLSPGERATLSCRASQYISSNYLAWYQ QKPGQAPRLLIYGASNRATGIPDRESGSGSGTDFTLTI SRLEPEDFAVYYCQQYSSDPITFGQGTKLEIK | 12 |
| L15 VH | EVQLVESGGGLVKPGGSLRLSCAASGFTFSSYSMNW VRQAPGKGLEWVSSISGQSNYIYYADSVKGRFTISRD NAKNSLYLQMNSLRAEDTAVYYCARGGNYFVEYFQ YWGQGTLVTVSS | 13 |
| L15 VL | EIVLTQSPGTLSLSPGERATLSCRASQYISSNNLAWYQ QKPGQAPRLLIYGASNRATGIPDRFSGSGSGTDFTLTI SRLEPEDFAVYYCQQYADSPITFGQGTKLEIK | 14 |
| M02 VH | EVQLVESGGGLVKPGGSLRLSCAASGFTFSSYSMNW VRQAPGKGLEWVSSISGQSNYIYYADSVKGRFTISRD NAKNSLYLQMNSLRAEDTAVYYCARGGNYYVEYFQ YWGQGTLVTVSS | 15 |
| M02 VL | EIVLTQSPGTLSLSPGERATLSCRASQYISSNNLAWYQ QKPGQAPRLLIYGASNRATGIPDRFSGSGSGTDFTLTI SRLEPEDFAVYYCQQYSSDPITFGQGTKLEIK | 16 |
| N22 VH | EVQLVESGGGLVKPGGSLRLSCAASGFTFSSYSMNW VRQAPGKGLEWVSSISGSSNYIYYADSVKGRFTISRD NAKNSLYLQMNSLRAEDTAVYYCARGGNYFVEYFQ YWGQGTLVTVSS | 17 |
| N22 VL | EIVLTQSPGTLSLSPGERATLSCRASQYISSNYLAWYQ QKPGQAPRLLIYGASNRATGIPDRESGSGSGTDFTLTI SRLEPEDFAVYYCQQYSSSPITFGQGTKLEIK | 18 |
| P10 VH | EVQLVESGGGLVKPGGSLRLSCAASGFTFRSYSMNW VRQAPGKGLEWVSSISGQSNYIYYADSVKGRFTISRD NAKNSLYLQMNSLRAEDTAVYYCARGGNYYVEYFQ YWGQGTLVTVSS | 19 |
| P10 VL | EIVLTQSPGTLSLSPGERATLSCRASQYISSNYLAWYQ QKPGQAPRLLIYGASNRATGIPDRESGSGSGTDFTLTI SRLEPEDFAVYYCQQYTDSPITFGQGTKLEIK | 20 |

The results of this example demonstrate the production of monoclonal antibodies directed against BCMA.

Example 2

This example demonstrates a method of producing an antibody-drug conjugate (ADC) comprising a BCMA monoclonal antibody conjugated to a cytotoxin in accordance with the present disclosure.

The 15B2GL monoclonal antibody and optimized clones described in Example 1 were conjugated to the PBD payload SG3249 using site specific conjugation (Thompson et al., J. Control Release, 236: 100-116 (2016); Dimasi et al. Mol Pharm. 2017 May 1; 14(5):1501-1516). Specifically, purified antibody was incubated with a 40 molar excess of the reducing agent TCEP (tris(hydroxymethyl)aminomethane (2 carboxyethyl)phosphine) in PBS pH 7.2, 1 mM EDTA (Ethylenediamine tetraacetic acid) for 3 hours at 37° C. After incubation, the reducing agent was removed by 2×dialysis in PBS pH 7.2, 1 mM EDTA at 4° C. using 10,000 MWCO dialysis cassettes, followed by incubation with 20 molar equivalents of dehydroascorbic acid for four hours at 25° C. Subsequently, eight equivalents of the PBD payload SG3249 from a stock solution in 10% (v/v) DMSO was sequentially added, followed by incubation at room temperature for one hour under gentle rotation. The conjugation reaction was quenched by the addition of four molar equivalents (over SG3249) of N-acetyl cysteine.

The conjugation process resulted in 8 to 10% of aggregate formation. Macromolecular aggregates, conjugation reagents, including cysteine quenched SG3249, were removed using ceramic hydroxyapatite Type II chromatography (CHT) as described previously (Thompson et al., *J. Control Release*, 236: 100-116 (2016)). Site-specific ADCs were formulated in 25 mM Histidine-HCl, 7% sucrose, 0.02% polysorbate-80, pH 6.

To determine monomeric content, aggregates, and fragments, analytical size-exclusion chromatography (SEC-HPLC) was performed using 100 μg (100 μL volume) of antibodies or ADCs, which were loaded into a TSKgel® G3000WXL column (Tosoh Bioscience, Tokyo, Japan). The mobile phase was composed of 0.1 M sodium sulfate, 0.1 M sodium phosphate, and 10% isopropanol, pH 6.8. The flow rate was 1 mL/min, and each analysis was carried out for 20 minutes at room temperature. Hydrophobic interaction chromatography (HIC-HPLC) was used to assess conjugation and drug load distribution, and was performed using a butyl-non porous resin (NPR) column (4.6 μm ID×3.5 cm, 2.5 μm, Tosoh Bioscience). The mobile phase A was composed of 25 mM tris(hydroxymethyl)aminomethane hydrochloride, 1.5 M $(NH_4)_2SO_4$, pH 8.0; and the mobile phase B was composed of 25 mM tris(hydroxymethyl)aminomethane hydrochloride and 5% isopropanol, pH 8.0. 100 μL of antibodies or ADCs at a concentration of 1 mg/mL were loaded and eluted at a flow rate of 1 mL/min with a gradient of 5% B to 100% B over 13 min. Reduced reverse phase chromatography (rRP-HPLC) was used to confirm chain-specific conjugation. The antibodies and ADCs were reduced at 37° C. for 20 minutes using 42 mM dithiothreitol (DTT) in PBS (pH 7.2). 10 μg of reduced antibodies or ADCs were loaded onto a polymeric reverse phase media (PLRP-S) 1000 A column (2.1×50 mm) (Agilent Technologies, Santa Clara, CA) and eluted at 80° C. at a flow rate of 1 mL/min with a gradient of 5% B to 100% B over 25 minutes (mobile phase A: 0.1% Trifluoroacetic acid in water; mobile phase B: 0.1% Trifluoroacetic acid in acetonitrile).

Conjugation at the heavy and light chains and drug: antibody ratios (DAR) were determined by reduced liquid chromatography mass spectrometry analysis (rLCMS) performed on an Agilent 1290 series uHPLC coupled to an Agilent 6230 TOF (Agilent Technologies, Santa Clara, Calif.). 2 μg of reduced antibodies or ADCs were loaded onto a ZORBAX® rapid resolution high definition (RRHD) 300-Diphenyl column (2.1×50 mm, 1.8 μm) (Agilent Technologies, Santa Clara, Calif.) and eluted at a flow rate of 0.5 mL/min using a step gradient of 80% B after 2.1 min (mobile phase A: 0.1% Formic acid in water and mobile phase B: 0.1% Formic acid in acetonitrile). A positive time-of-flight MS scan was acquired, and data collection and processing were carried out using MassHunter software (Agilent Technologies, Santa Clara, Calif.). DAR was calculated using the rLCMS data as described in Thompson et al., supra.

Efficiency of conjugation was determined using the following equation, where a theoretical DAR of 2 was used:

Efficiency of conjugation=(Determined DAR×Theoretical DAR)×1/100

Conjugation efficiencies and DARs of the tested antibodies are set forth in Table 2.

TABLE 2

| Construct name | Payload | Conjugation Efficiency | Drug: Antibody Ratio (DAR) |
|---|---|---|---|
| 15B2GL | SG3249 | 91 | 1.82 |
| I09 | SG3249 | 91 | 1.82 |
| L15 | SG3249 | 90 | 1.80 |
| M02 | SG3249 | 92 | 1.84 |
| N22 | SG3249 | 91 | 1.82 |
| P10 | SG3249 | 93 | 1.86 |

The results of this example demonstrate the production of ADCs comprising a BCMA monoclonal antibody conjugated to a pyrrolobenzodiazepine in accordance with the present disclosure.

Example 3

This example demonstrates the binding affinity of monoclonal BCMA antibodies described herein to monomeric (soluble) and membrane-bound BCMA.

The binding of 15B2GL monoclonal antibody and optimized clones I09, L15, P10, N22, and M02 (described in Example 1) was assessed using monomeric human sBCMA (GenScript, Piscataway, N.J.) using a ProteOn™ XPR36 instrument (Bio-Rad, Hercules, Calif.). The binding of J6M0 also was assessed for comparison. Standard amine coupling was used to immobilize 25 μg/ml anti-Fc polyclonal antibody (Jackson ImmunoResearch, West Grove, Pa.) prepared in 10 mM sodium acetate buffer (pH 4.5) to the surface of a ProteOn™ GLC biosensor chip (Bio-Rad, Hercules, Calif.) pre-activated with 20 mM EDAC (1-ethyl-3-(3-dimethylaminopropyl)carbodiimide hydrochloride) and 5 mM Sulfo-NHS (N-hydroxysulfosuccinimide) at a density of ~200-600 resonance units (RU). 15B2GL, I09, L15, P10, N22, M02, and J6M0 were subsequently injected at a concentration of 1 μg/ml for capture by the immobilized anti-Fc polyclonal antibody. The sensorgram was recorded by flowing two-fold serial dilutions of sBCMA prepared in PBS (pH 7.4) with 0.005% (v/v) Tween®-20, ranging from 100-6.25 nM, over the captured surface for 150 seconds at 75 μL/minute with dissociation time of 600 seconds. ProteOn™ data analysis software was used to analyze the data.

The results of this experiment are shown in FIGS. 13 and 14 and Table 3.

TABLE 3

| Kinetics measurements using BioRad ProteOn ™ | | | | |
|---|---|---|---|---|
| Antibody | Kon | Koff | Kd | nM |
| 15B2GL | 3.73E+05 | 2.27E−02 | 6.07E−08 | 60.7 |
| N22 | 5.36E+05 | 8.73E−03 | 1.63E−08 | 16 |
| I09 | 6.09E+05 | 5.99E−03 | 9.82E−09 | 9.8 |
| M02 | 4.99E+05 | 4.97E−03 | 9.95E−09 | 9.9 |
| L15 | 8.54E+05 | 3.86E−03 | 4.51E−09 | 4.5 |
| P10 | 7.01E+05 | 3.73E−03 | 5.32E−09 | 5.3 |
| J6M0 | 4.21E+05 | 4.69E−04 | 1.11E−09 | 1 |

Binding of 15B2GL, I09, L15, and J6M0 to membrane-bound human BCMA was evaluated using flow cytometry in multiple myeloma and plasma cell leukemia cell lines that endogenously express BCMA (NCI-H929 and MM.1S, respectively). Binding of 15B2GL, I09, L15 to membrane-bound human BCMA was also evaluated in Ad293 cells expressing human BCMA. Binding assays were performed by incubating the anti-BCMA antibodies with 200,000 cells for 30 minutes at 4° C. followed by two washes with PBS+2% FBS (FACS Buffer). A range of antibody concentrations were evaluated using a 12-point, 3-fold dilution series. Cells were then incubated with 5 ug/mL goat-anti human IgG-AF647 secondary antibodies (Thermo Fisher Scientific, Waltham, Mass.) at 4° C., followed by two washes in PBS+2% FBS. Cells were resuspended in 200 uL PBS+2% FBS+DAPI.

Fluorescence of live, single cells was measured using a BD Biosciences LSRII cytometer and BD FACSDiva™ software (BD Biosciences, San Jose, Calif.). Data were analyzed using FlowJo™ software (FlowJo, LLC, Ashland, Oreg.). Mean fluorescence intensity values were used to determine percentage bound and EC50 was determined using Prism™ software (GraphPad Software Inc, La Jolla, Calif.). The results of this experiment are shown in FIG. 15. A summary of the SPR and flow cytometry "apparent affinity" data is shown in Table 4.

TABLE 4

| Antibody | Binding Affinity (nM), monomeric BCMA | Apparent affinity (nM), cell-bound BCMA | | |
|---|---|---|---|---|
| | | NCI-H929 | MM.1S | Ad293 + huBCMA |
| 15B2GL | 60.7 | 3.14 | 2.56 | 3.87 |
| N22 | 16 | ND | ND | ND |
| I09 | 9.8 | 5.4 | 4.8 | 5.3 |
| M02 | 9.9 | ND | ND | ND |
| L15 | 4.5 | 4.2 | 4.2 | 4.48 |
| P10 | 5.3 | ND | ND | ND |
| J6M0 | 1 | 6.02 | 6.65 | ND |

ND = not determined

The results of this example demonstrate that monoclonal anti-BCMA antibody 15B2GL binds strongly to membrane-bound BCMA and weakly to monomeric (soluble) BCMA, which is unique from the other monoclonal antibodies that were analysed in these assays.

Example 4

This example demonstrates methods of killing multiple myeloma and plasma cell leukemia cells in vitro using the antibody-drug conjugates described herein.

Killing of multiple myeloma and plasma cell leukemia cell lines by antibody-drug conjugates comprising 15B2GL, or affinity-optimized clones thereof, conjugated to SG3249 was evaluated in vitro using the protocol recommended in the CELLTITER-GLO® kit (Promega, Madison, Wis.). Killing of multiple myeloma and plasma cell leukemia cell lines by the free warhead SG3199 also was evaluated using the protocol recommended in the CELLTITER-GLO® kit (Promega, Madison, Wis.). Briefly, $5 \times 10^3$ cells in 80 μL RPMI+10% FBS were added to the inner wells of white-walled 96-well plates (Corning® Costar®, Fisher Scientific, Waltham, Mass.). The following BCMA-expressing cell lines were tested: NCI-H929, EJM, MM.1R. JJN3, OPM-2, MM.1S, U266.B1, and L363. BMCA-negative cell lines Raji and Jurkat also were tested. The antibody-drug conjugates were diluted to a 5× stock (2.5 μg/mL) in RPMI+10% FBS. Treatments were then serially diluted 1:3 in RPMI+ 10% FBS. 20 μL of this series was added to the cells in duplicate, resulting in a 12-point dose curve of antibody-drug conjugate ranging from 0.5 μg/mL at the highest concentration to $3 \times 10^{-6}$ vg/mL at the lowest. Isotype antibody-drug conjugate (IgG1-SG3249 and IgG1-mc-MMAF) and media-only controls also were included. Plates were incubated at 37° C., 5% $CO_2$ for 96 hours. At the end of the incubation period, 100 μL of the Substrate Solution (Promega, Madison Wis.) was added to each well. Luminescence was measured using an EnVision™ Multilabel plate reader (Perkin Elmer, Waltham, Mass.). Data were analyzed and graphed using GraphPad Prism™ software (GraphPad Software, Inc., La Jolla, Calif.), and the half-maximal inhibitory concentration (IC50) was determined.

Chromosomal translocation information for each cell line was taken from Moreaux et al, 2011 and Boersma-Vreugdenhil et al, 2004. BCMA receptor number was determined using AF647-labeled 15B2 (Alexa Fluor® 647 Protein Labeling kit, Thermo Fisher Scientific, Waltham, MA) and the Quantum™ MESF kit for Alexa Fluor® 647 (Bangs Laboratories, Fishers, IN).

The results of this experiment are shown in Table 5 and FIGS. 2A-2J.

TABLE 5

In vitro cytotoxicity in multiple myeloma and plasma cell leukemia cell lines

| Cell line | Disease Origin | Chromosomal Translocation | BCMA receptor number | 15B2GL-SG3249 IC50 (ng/ml) | SG3199 IC50 (pM) |
|---|---|---|---|---|---|
| NCI-H929 | MM | t(4;14) | 18931 | 5.99 | 5 |
| EJM | MM | t(14;20) | 14325 | 153 | 22 |
| MM.1R | PCL | t(14;16) | 9449 | 8.64 | 3 |
| JJN-3 | MM | t(14;16) | 3221 | 36.28 | 13 |
| OPM-2 | MM | t(4;14) | 2873 | 201 | 19 |
| MM.1S | PCL | t(14;16) | 2698 | 26.8 | 3 |
| U266B1 | MM | t(11;14) | 2340 | 39.7 | 155 |
| L-363 | PCL | t(20;22) | 930 | 31.4 | NT |
| Raji | Burkitt's lymphoma | NA | 0 | >500 | NT |
| Jurkat | T-lymphocyte | NA | 0 | >500 | 3 |

BCMA = B-cell maturation antigen; NA = not applicable; NT = not tested

The ability of the 15B2GL-SG3249 ADC to kill multiple myeloma cells in vitro in the presence of soluble BCMA (sBCMA) as compared to the I09-5G3249 ADC was evaluated in MM.1S cells using the protocol described above, except that tested cell lines also were treated with BCMA-containing conditioned media collected from Ad293 cells expressing human BCMA (FIGS. 3A and 3B). 15B2GL-SG3249 ADC cell killing in the presence of sBCMA also was compared to ADCs comprising the anti-BCMA antibody J6M0, which is described in U.S. Pat. No. 9,273,141. The results of this experiment are shown in FIG. 3, which demonstrates that 15B2GL-SG3249 ADC activity is maintained in the presence of clinically-relevant levels of sBCMA to a greater degree than ADCs I09-5G3249 (FIG. 3A), J6M0-mc-MMAF, and J6M0-SG3249 (FIG. 3B and Table 6).

TABLE 6

| sBCMA (ng/mL) | Test Article | IC50 (ng/mL) | Fold loss of potency |
|---|---|---|---|
| 720 | 15B2GL-SG3249 | 29.12 | 2.01 |
| 270 | 15B2GL-SG3249 | 22.86 | 1.58 |
| 75 | 15B2GL-SG3249 | 16.09 | 1.11 |
| 0 | 15B2GL-SG3249 | 14.47 | 1.00 |
| 720 | J6M0-SG3249 | 92.92 | 19.29 |
| 270 | J6M0-SG3249 | 32.26 | 6.70 |
| 75 | J6M0-SG3249 | 12.83 | 2.66 |
| 0 | J6M0-SG3249 | 4.816 | 1.00 |
| 720 | I09-SG3249 | 16.16 | 5.75 |

TABLE 6-continued

| sBCMA (ng/mL) | Test Article | IC50 (ng/mL) | Fold loss of potency |
|---|---|---|---|
| 270 | I09-SG3249 | 5.548 | 1.98 |
| 75 | I09-SG3249 | 3.791 | 1.35 |
| 0 | I09-SG3249 | 2.809 | 1.00 |
| 720 | J6M0-mc-MMAF | 1458 | 49.80 |
| 270 | J6M0-mc-MMAF | 159.7 | 5.45 |
| 75 | J6M0-mc-MMAF | 55.55 | 1.90 |
| 0 | J6M0-mc-MMAF | 29.28 | 1.00 |

The results of this example demonstrate that the 15B2GL-SG3249 ADC kills multiple myeloma and plasma cell leukemia cells in vitro, and that the cell-killing activity is maintained even in the presence of soluble BCMA. In particular, the 15B2GL-SG3249 ADC was cytotoxic to both MM.1S and NCI-H929 in vitro, killing an average of 95% of tumor cells in the presence of sBCMA at levels up to 720 ng/mL with little impact on IC50. ADCs developed from antibodies that possessed a similar affinity between monomeric BCMA and membrane-bound BCMA exhibited a sBCMA-dose dependent drop in potency, with a 20-fold shift in IC50 in the presence of 720 ng/mL sBCMA.

Example 5

This example demonstrates methods of killing multiple myeloma and plasma cell leukemia cells in vivo using the antibody-drug conjugates described herein.

Subcutaneous xenograft mouse models of multiple myeloma and plasma cell leukemia were generated by implanting BCMA-expressing multiple myeloma or plasma cell leukemia cell lines (i.e., NCI-H929, JJN-3, MM.1S, and MM.1R) into female CB-17 SCID (C.B-17/IcrHsd-Prkdc-scid) or athymic nude (Foxn1$^{nu}$) mice using MATRIGEL™ (BD Biosciences, San Jose, Calif.). Once tumors reached approximately 180 mm$^3$ (NCI-H929 cells), 190 mm$^3$ (JJN3 cells), 160 mm$^3$ (MM.1S cells), or 175 mm$^3$ (MM.1R cells), mice were randomized based on tumor size and placed into dosing groups and treated with BCMA-targeting ADCs as described below.

NCI-H929 Xenograft Model

Mice were treated with either a single intravenous dose of the ADCs 15B2GL-SG3249, I09-5G3249, L15-SG3249 at 0.3 mg/kg or dosed intravenously with J6M0-mc-MMAF weekly at a dose of 0.3 mg/kg for 2 weeks. Control mice were left untreated. Mice treated with 15B2GL-SG3249, I09-5G3249, and L15-SG3249 were observed for 99 days post tumor implantation with no evidence of tumor regrowth, as shown in FIG. 4. No body weight loss was observed in any of the dosing groups.

JJN3 Xenograft Model

Mice were treated with either a single intravenous dose of 15B2GL-SG3249, I09-SG3249, and L15-SG3249 ADCs at 1 mg/kg, or dosed intravenously with J6M0-mc-MMAF ADC weekly at a dose of 1 mg/kg for 3 weeks. Control mice were left untreated. Mice treated with 15B2GL-SG3249, I09-5G3249, and L15-SG3249 were observed for 104 days post tumor implantation with no evidence of tumor regrowth, as shown in FIG. 5. No body weight loss was observed in any of the dosing groups.

MM.1S Xenograft Model

Mice were treated with either a single intravenous dose of 15B2GL-SG3249, I09-SG3249, L15-SG3249 ADCs at 1 mg/kg or dosed intravenously with J6M0-mc-MMAF twice weekly at a dose of 1 mg/kg for 4 weeks. Control mice were left untreated. Mice treated with 15B2GL-SG3249, I09-5G3249, and L15-SG3249 were observed for 99 days post tumor implantation with no evidence of tumor regrowth, as shown in FIG. 6. No body weight loss was observed in any of the dosing groups.

MM.1R Xenograft Model

Mice were treated with either a single intravenous dose of 15B2GL-SG3249 at 1 mg/kg or dosed intravenously with J6M0-mc-MMAF weekly at a dose of 3 mg/kg for 4 weeks. Control mice were left untreated. Mice treated with 15B2GL-SG3249 were observed for 109 days post tumor implantation with no evidence of tumor regrowth, as shown in FIG. 7. No body weight loss was observed in any of the dosing groups.

The results of this example demonstrate that the ADC 15B2GL-SG3249 exhibits increased anti-tumor efficacy in vivo as compared to other ADCs which target BCMA-expressing cells.

Example 6

This example demonstrates that multiple myeloma stem cells express BCMA.

The bone marrow of multiple myeloma (MM) patients contains a small population of cancer stem cells (CSCs) that can be identified in the bone marrow of patients by their surface expression of CD19 and lack of CD138 surface expression (Matsui et al., *Blood*, 103: 2332-6 (2004)).

BCMA expression was evaluated on the stem cell population of four multiple myeloma patient samples by flow cytometry. Samples were acquired from Proteogenex, Inc. (Culver City, Calif.) (see Table 7), and individual multiple myeloma (MM) samples were thawed in a 37° C. water bath.

TABLE 7

MM Patient information.

| Sample ID | Sex | Age | Ethnicity | Clinical diagnosis | Disease status |
|---|---|---|---|---|---|
| MM263BM | M | 63 | Caucasian | MM | at diagnosis |
| MM277BM | F | 66 | Caucasian | MM | at diagnosis |
| MM276BM | F | 81 | Caucasian | MM | at diagnosis |
| MM284BM | M | 84 | Caucasian | MM | resistant to therapy |

The thawed cells were added to 10 mL of PBS and were counted using a ViCELL™ counter (Beckmann-Coulter Life Sciences, Indianapolis, IN). An aliquot of the cell suspension was prepared for a colony formation assay, while the remainder of the cell suspension was centrifuged at low speed to pellet the cells. Cells were Fc blocked following the manufacturer's instructions, then plated at 200,000 cells per well in a 96-well plate. The plate was centrifuged to pellet cells, Fc block solution decanted, and cell samples were resuspended in BV staining buffer followed by staining with an appropriate antibody panel comprised of commercially sourced directly conjugated antibodies, which are shown in Tables 8 and 9.

TABLE 8

Antibody staining panel

| Sample | Description | Antibody Panel |
|---|---|---|
| 1 | single stain BV510 | CD3-BV510, CD34-BV510, CD14-BV510, CD193-BV510 |
| 2 | single stain PE | CD138-PE |

TABLE 8-continued

Antibody staining panel

| Sample | Description | Antibody Panel |
|---|---|---|
| 3 | single stain APC | CD19-APC |
| 4 | single stain PE-Cy7 ® | BCMA-PE-Cy7 ® |
| 5 | Unstained | |
| 6 | single stain DAPI | DAPI |
| 7 | FMO (BV510) | CD138-PE, CD19-APC, BCMA-PE-Cy7 ®, DAPI |
| 8 | FMO (PE) | CD3-BV510, CD34-BV510, CD14-BV510, CD193-BV510, CD19-APC, BCMA-PE-Cy7 ®, DAPI |
| 9 | FMO (APC) | CD3-BV510, CD34-BV510, CD14-BV510, CD193-BV510, CD138-PE, BCMA-PE-Cy7 ®, DAPI |
| 10 | FMO (PE-Cy7 ®) | CD3-BV510, CD34-BV510, CD14-BV510, CD193-BV510, CD138-PE, CD19-APC, DAPI |
| 11 | all stains | CD3-BV510, CD34-BV510, CD14-BV510, CD193-BV510, CD138-PE, CD19-APC, BCMA-PE-Cy7 ®, DAPI |
| 12 | FMO (DAPI) | CD3-BV510, CD34-BV510, CD14-BV510, CD193-BV510, CD138-PE, CD19-APC, BCMA-PE-Cy7 ® |
| 13 | compensation beads BV510 | CD193-BV510 |
| 14 | compensation beads PE | CD138-PE |
| 15 | compensation beads APC | CD19-APC |
| 16 | compensation beads PE-Cy7 ® | BCMA-PE-Cy7 ® |

TABLE 9

Antibodies used for flow cytometry analysis

| Antibody/Reagent | Clone | Vendor | Cat# |
|---|---|---|---|
| CD3-BV510 | OKT3 | Biolegend | 317332 |
| CD34-BV510 | 581 | Biolegend | 343528 |
| CD14-BV510 | M5E2 | Biolegend | 301842 |
| CD193-BV510 | 5E8 | Biolegend | 310722 |
| CD19-APC | SJ25C1 | BD Biosciences | 340437 |
| CD138-PE | B-A38 | Beckman Coulter | A40316 |
| BCMA-PE-Cy7 ® | 19F2 | Biolegend | 357508 |
| DAPI | | ThermoFisher Scientific | 62248 |
| FC Block ™ | | BD Pharmingen | 564220 |
| BD Horizon ™ Brilliant Stain Buffer | | BD Biosciences | 563794 |
| UltraComp eBEADS ™ | | eBiosciences | 01-2222-42 |

In addition, compensation beads were stained individually with test antibodies. The plate was incubated at 4° C. in the dark for 30 minutes. The plate was centrifuged and cells were washed in DPBS+2% FBS, followed by resuspension in 200 μL DPBS+2% FBS+DAPI. Cells from each well were assessed on a BD LSRII flow cytometer (BD Biosciences, San Jose, Calif.) and FCS files were generated. Cell identification was performed using the following gating strategy: compensation was performed with the auto comp matrix in FlowJo®10 (FlowJo LLC, Ashland, Oreg.), utilizing the compensation bead and single stain data. Plasma cells gated through the FSC-A vs SSC-A plot were then selected for live, single cells through the DAPI vs SSC-W plot. An exclusion gate was then used to remove cells that stained positive for CD3, CD14, CD34, and CD193 through the BV-510 vs SSC-A plot. This population was then analyzed in the CD138-PE vs CD19-APC plot. Histograms for BCMA expression were generated on the MM CSC population defined as CD19+/CD138−, and the MM plasma cell population defined as CD19−/CD138+. Analysis gates were set based on the appropriate fluorescence minus one (FMO) controls. All samples showed a small percentage of CD138+ CD19− cells that were positive for BCMA expression, as shown in FIG. 7. The level of BCMA expression on the stem cell population was generally equal to the level observed on the plasma cells, except for MM277, where the level was lower but still positive for BCMA expression.

The results of this example demonstrate that BCMA is expressed on multiple myeloma cancer stem cells.

Example 7

This example demonstrates that the 15B2GL-SG3249 antibody-drug conjugate kills multiple myeloma stem cells.

As MM stem cells are capable of forming colonies in vitro (Matsui et al., *Blood*, 103: 2332-6 (2004)), the ability of the ADC 15B2GL-SG3249 to kill the clonogenic cells in the MM bone marrow biopsies characterized in Example 2 was tested. In particular, cells were counted using a ViCELL™ counter (Beckmann-Coulter Life Sciences, Indianapolis, Ind.) and resuspended in IMDM+2% FBS at 10-fold higher density than required for plating. METHOCULT™ H4434 Classic (StemCell Technologies, Inc., Vancouver, BC, Canada) was mixed with 2000 cells per mL for MM263, MM284, and MM276, and 4000 cells per mL for MM277 following the manufacturer's instructions. 25-400 ng per mL of the test ADCs 15B2GL-SG3249 and J6M0-mc-MMAF was then added to appropriate tubes. A control IgG1-SG3249 antibody was added at only the high dose of 400 ng per mL. All tubes were vortexed thoroughly to mix and then allowed to sit undisturbed, allowing air bubbles to rise to the top. Once the bubbles had risen, 400 μL was removed with a 16-guage blunt end needle and carefully plated into one well of a 24-well ultralow attachment plate (VWR, Radnor, Pa.). Each treatment was plated in duplicate in the inner wells of the plate. PBS was added to the outer wells and the plate was incubated at 37° C. for 7-10 days. Colonies were counted by eye with documentation of colony formation by scanning plates on a Celigo® Image Cytometer (Nexcelom Biosciences, Lawrence, Mass.). As shown in FIG. 8, in all 4 cases, 15B2GL-SG3249 was able to kill the clonogenic cells, while J6M0-mc-MMAF was not. At the highest dose tested (400 ng/mL), 15B2GL-SG3249 was able to kill 100% of the colonies for MM263 and MM284 and 87.5% and 91% of the colonies for MM276 and MM277, respectively. In contrast, 400 ng/mL of J6M0-mc-MMAF did not reduce the number of colonies formed for MM263, and only resulted in a 12.5%, 40%, and 50% reduction in colony formation for MM276, MM277, and MM284, respectively.

The results of this example demonstrate that the antibody-drug conjugate 15B2GL-SG3249 targets and kills BCMA-expressing multiple myeloma cancer stem cells.

Example 8

This example demonstrates methods of killing multiple myeloma and plasma cell leukemia cells in vitro using the antibody-drug conjugates described herein.

Killing of multiple myeloma and plasma cell leukemia cell lines by antibody-drug conjugates comprising 15B2GL conjugated to SG3400 was evaluated in vitro using the CELLTITER-GLO® kit (Promega, Madison, Wis.), as described in Example 4. The following BCMA-expressing cell lines were tested: NCI-H929, EJM, MM.1R. JJN3, OPM-2, MM.1S, U266.B1, and L363. BMCA-negative cell lines Raji and Jurkat also were tested. The antibody-drug conjugates were diluted to a 5× stock (25 µg/mL) in RPMI+ 10% FBS. Treatments were then serially diluted 1:3 in RPMI+10% FBS. 20 µL of this series was added to the cells in duplicate, resulting in a 12-point dose curve of antibody-drug conjugate ranging from 5 µg/mL at the highest concentration to $2.8 \times 10^{-5}$ µg/mL at the lowest. Isotype antibody-drug conjugate (IgG1-SG3400) and media-only controls also were included. Plates were incubated at 37° C., 5% $CO_2$ for 96 hours. At the end of the incubation period, 100 µL of the Substrate Solution (Promega, Madison Wis.) was added to each well. Luminescence was measured using an EnVision™ Multilabel plate reader (Perkin Elmer, Waltham, Mass.). Data were analyzed and graphed using GraphPad Prism™ software (GraphPad Software, Inc., La Jolla, Calif.). The results of this experiment are shown in FIGS. 10A-10J.

The results of this example demonstrate that the 15B2GL-SG3400 ADC kills multiple myeloma and plasma cell leukemia cells in vitro.

Example 9

This example demonstrates methods of killing multiple myeloma and plasma cell leukemia cells in vivo using the antibody-drug conjugates described herein.

Subcutaneous xenograft mouse models of multiple myeloma and plasma cell leukemia were generated by implanting BCMA-expressing multiple myeloma or plasma cell leukemia cell lines (i.e., NCI-H929 and MM.1S) into female CB-17 SCID (C.B-17/IcrHsd-Prkdc-scid) mice using MATRIGEL™ (BD Biosciences, San Jose, Calif.). Once tumors reached approximately 200 mm³ (NCI-H929 cells) or 180 mm³ (MM.1S cells), mice were randomized based on tumor size and placed into dosing groups and treated with BCMA-targeting ADCs as described below.

NCI-H929 Xenograft Model

Mice were treated with either a single intravenous dose of the ADCs IgG1-SG3400 at 1 mg/kg or 15B2GL-SG3400 at 0.3 mg/kg or 1 mg/kg or dosed intravenously with J6M0-SG3400 with a single dose of 0.3 mg/kg or 1 mg/kg. Control mice were left untreated. Mice treated with 15B2GL-SG3400 were observed for 74 days post tumor implantation with no evidence of tumor regrowth, as shown in FIG. 11. No body weight loss was observed in any of the dosing groups.

MM.1S Xenograft Model

Mice were treated with either a single intravenous dose of the ADCs IgG1-SG3400 or 15B2GL-SG3400 at 1 mg/kg or 3 mg/kg or dosed intravenously with J6M0-SG3400 at a dose of 1 mg/kg or 3 mg/kg. Control mice were left untreated. Mice treated with 3 mg/kg of J6M0-SG3400 were observed for 85 days post tumor implantation with no evidence of tumor regrowth, as shown in FIG. 12. No body weight loss was observed in any of the dosing groups.

The results of this example demonstrate that the ADC 15B2GL-SG3400 exhibits anti-tumor efficacy in vivo.

The data described in the Examples demonstrate that an ADC comprising monoclonal antibody 15B2GL exhibits potent antitumor activity in preclinical models of MM. Importantly, in vitro experiments suggest that this activity is maintained in the presence of sBCMA. These data further demonstrate that the ADC 15B2GL-SG3249, bearing a potent PBD payload, effectively targets both the bulk myeloma plasma cells as well as the more quiescent, CD19+/CD138− clonogenic cells, which may offer an opportunity for more durable clinical response in this genetically heterogeneous disease.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

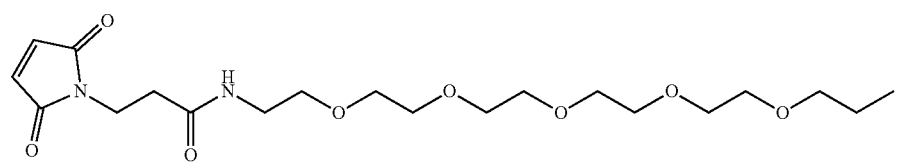

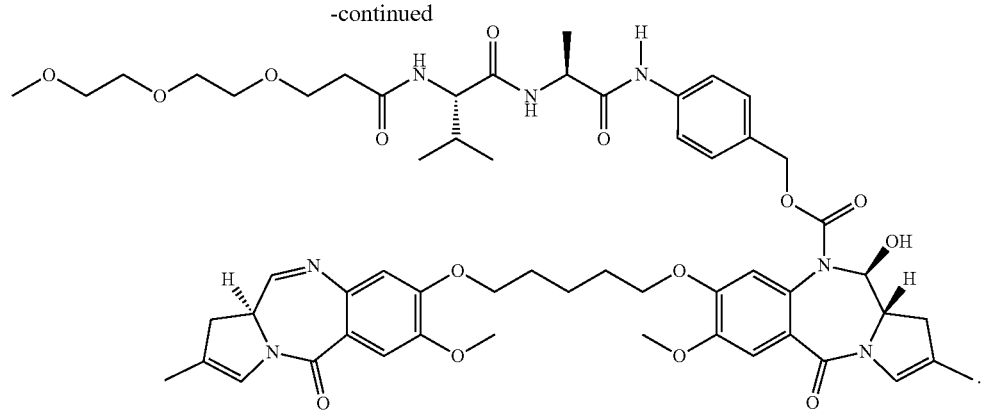

The invention claimed is:

1. A method of killing multiple myeloma cells comprising:
   contacting multiple myeloma cells that express B-cell maturation antigen (BCMA) with an antibody-drug conjugate (ADC) comprising a monoclonal antibody, or an antigen-binding fragment thereof, directed against BCMA conjugated to a cytotoxin, wherein the monoclonal antibody comprises
   (a) a heavy chain variable region comprising a complementarity determining region 1 (HCDR1) amino acid sequence of SEQ ID NO: 1, an HCDR2 amino acid sequence of SEQ ID NO: 2, and an HCDR3 amino acid sequence of SEQ ID NO: 3; and
   (b) a light chain variable region comprising a complementarity determining region 1 (LCDR1) amino acid sequence of SEQ ID NO: 4, an LCDR2 amino acid sequence of SEQ ID NO: 5, and an LCDR3 amino acid sequence of SEQ ID NO: 6;
   wherein the ADC binds to BCMA on the multiple myeloma cells and kills the multiple myeloma cells.

2. The method of claim 1, wherein the ADC is in a composition with a pharmaceutically acceptable carrier.

3. The method of claim 1, wherein the multiple myeloma cells are in a human.

4. The method of claim 1, wherein the multiple myeloma cells are in vitro.

5. The method of claim 1, wherein the heavy chain variable region comprises the amino acid sequence of SEQ ID NO: 7.

6. The method of claim 1, wherein the light chain variable region comprises the amino acid sequence of SEQ ID NO: 8.

7. The method of claim 1, wherein the heavy chain variable region comprises the amino acid sequence of SEQ ID NO: 7 and the light chain variable region comprises the amino acid sequence of SEQ ID NO: 8.

8. The method of claim 1, wherein the cytotoxin is an anti-microtubule agent, a pyrrolobenzodiazepine (PBD), an RNA polymerase II inhibitor, or a DNA alkylating agent.

9. The method of claim 8, wherein the cytotoxin is an anti-microtubule agent selected from the group consisting of a maytansinoid, an auristatin, and a tubulysin.

10. The method of claim 8, wherein the cytotoxin is a pyrrolobenzodiazepine (PBD).

11. The method of claim 10, wherein the pyrrolobenzodiazepine is SG3249 having the following formula:

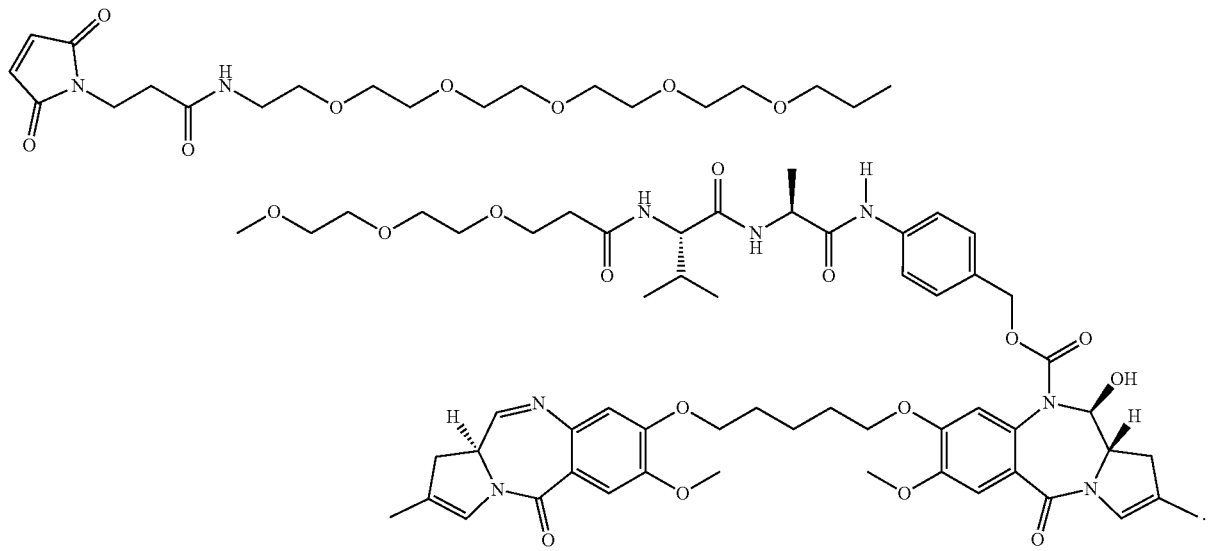

12. The method of claim 3, wherein the human has multiple myeloma and wherein a therapeutically effective amount of the ADC is administered to the human.

13. A method of killing multiple myeloma stem cells, comprising:
   contacting multiple myeloma stem cells that express B-cell maturation antigen (BCMA) with an antibody-drug conjugate (ADC) comprising a monoclonal antibody, or an antigen-binding fragment thereof, directed against BCMA conjugated to a cytotoxin, wherein the monoclonal antibody comprises
   (a) a heavy chain variable region comprising a complementarity determining region 1 (HCDR1) amino acid sequence of SEQ ID NO: 1, an HCDR2 amino acid sequence of SEQ ID NO: 2, and an HCDR3 amino acid sequence of SEQ ID NO: 3; and
   (b) a light chain variable region comprising a complementarity determining region 1 (LCDR1) amino acid sequence of SEQ ID NO: 4, an LCDR2 amino acid sequence of SEQ ID NO: 5, and an LCDR3 amino acid sequence of SEQ ID NO: 6;
   wherein the ADC binds to BCMA on the multiple myeloma stem cells and kills the multiple myeloma stem cells.

14. The method of claim 13, wherein the ADC is in a composition with a pharmaceutically acceptable carrier.

15. The method of claim 13, wherein the heavy chain variable region comprises the amino acid sequence of SEQ ID NO: 7 and the light chain variable region comprises the amino acid sequence of SEQ ID NO: 8.

16. The method of claim 13, wherein the cytotoxin is an anti-microtubule agent, a pyrrolobenzodiazepine (PBD), an RNA polymerase II inhibitor, or a DNA alkylating agent.

17. The method of claim 16, wherein the cytotoxin is an anti-microtubule agent selected from the group consisting of a maytansinoid, an auristatin, and a tubulysin.

18. The method of claim 16, wherein the cytotoxin is a pyrrolobenzodiazepine (PBD).

19. The method of claim 18, wherein the pyrrolobenzodiazepine is SG3249 having the following formula:

SEQUENCE LISTING

<160> NUMBER OF SEQ ID NOS: 20

<210> SEQ ID NO 1
<211> LENGTH: 5

```
<212> TYPE: PRT
<213> ORGANISM: Artificial Sequence
<220> FEATURE:
<223> OTHER INFORMATION: Synthetic

<400> SEQUENCE: 1

Ser Tyr Ser Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Ser Ile Ser Gly Ser Ser Asn Tyr Ile Tyr Tyr Ala Asp Ser Val Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: Synthetic

<400> SEQUENCE: 3

Gly Gly Asn Tyr Tyr Val Glu Tyr Phe Gln Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Arg Ala Ser Gln Tyr Ile Ser Ser Asn Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Gly Ala Ser Asn Arg Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Gln Gln Tyr Gly Ser Ser Pro Ile Thr
1               5

<210> SEQ ID NO 7
```

```
<211> LENGTH: 120
<212> TYPE: PRT
<213> ORGANISM: Artificial Sequence
<220> FEATURE:
<223> OTHER INFORMATION: Synthetic

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Ser Met Asn Trp Val Arg Gln Ala Pro Gly Lys Gly Leu Glu Trp Val
        35                  40                  45

Ser Ser Ile Ser Gly Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Tyr Tyr Val Glu Tyr Phe Gln Tyr Trp Gly Gln
            100                 105                 110

Gly Thr Leu Val Thr Val Ser Ser
        115                 120

<210> SEQ ID NO 8
<211> LENGTH: 108
<212> TYPE: PRT
<213> ORGANISM: Artificial Sequence
<220> FEATURE:
<223> OTHER INFORMATION: Synthetic

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Tyr Ile Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Lys Leu Glu Ile Lys
            100                 105

<210> SEQ ID NO 9
<211> LENGTH: 120
<212> TYPE: PRT
<213> ORGANISM: Artificial Sequence
<220> FEATURE:
<223> OTHER INFORMATION: Synthetic

<400> SEQUENCE: 9

Glu Ile Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30
```

Ser Met Asn Trp Val Arg Gln Ala Pro Gly Lys Gly Leu Glu Trp Val
            35                  40                  45

Ser Ser Ile Ser Gly Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Gly Asn Tyr Tyr Val Glu Tyr Phe Gln Tyr Trp Gly Gln
            100                 105                 110

Gly Thr Leu Val Thr Val Ser Ser
            115                 120

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Tyr Ile Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Gly Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Ile Thr Phe Gly Gln Gly Thr Lys Leu Glu Ile Lys
            100                 105

<210> SEQ ID NO 11
<211> LENGTH: 120
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Ser Ile Ser Gly Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Tyr Phe Val Glu Tyr Phe Gln Gln Trp Gly Gln
            100                 105                 110

Gly Thr Leu Val Thr Val Ser Ser
        115                 120

<210> SEQ ID NO 12
<211> LENGTH: 108
<212> TYPE: PRT
<213> ORGANISM: Artificial Sequence
<220> FEATURE:
<223> OTHER INFORMATION: Synthetic

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Tyr Ile Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Asp Pro
                85                  90                  95

Ile Thr Phe Gly Gln Gly Thr Lys Leu Glu Ile Lys
            100                 105

<210> SEQ ID NO 13
<211> LENGTH: 120
<212> TYPE: PRT
<213> ORGANISM: Artificial Sequence
<220> FEATURE:
<223> OTHER INFORMATION: Synthetic

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Gly Gln Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Tyr Phe Val Glu Tyr Phe Gln Tyr Trp Gly Gln
            100                 105                 110

Gly Thr Leu Val Thr Val Ser Ser
        115                 120

<210> SEQ ID NO 14
<211> LENGTH: 108
<212> TYPE: PRT
<213> ORGANISM: Artificial Sequence
<220> FEATURE:
<223> OTHER INFORMATION: Synthetic

<400> SEQUENCE: 14

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Tyr Ile Ser Ser Asn
            20                  25                  30

Asn Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Lys Leu Glu Ile Lys
            100                 105
```

<210> SEQ ID NO 15
<211> LENGTH: 120
<212> TYPE: PRT
<213> ORGANISM: Artificial Sequence
<220> FEATURE:
<223> OTHER INFORMATION: Synthetic

<400> SEQUENCE: 15

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Gly Gln Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Tyr Tyr Val Glu Tyr Phe Gln Tyr Trp Gly Gln
            100                 105                 110

Gly Thr Leu Val Thr Val Ser Ser
        115                 120
```

<210> SEQ ID NO 16
<211> LENGTH: 108
<212> TYPE: PRT
<213> ORGANISM: Artificial Sequence
<220> FEATURE:
<223> OTHER INFORMATION: Synthetic

<400> SEQUENCE: 16

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Tyr Ile Ser Ser Asn
            20                  25                  30

Asn Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

-continued

Pro Glu Asp Phe Ala Val Tyr Tyr Cys Gln Gln Tyr Ser Ser Asp Pro
                85                  90                  95

Ile Thr Phe Gly Gln Gly Thr Lys Leu Glu Ile Lys
            100                 105

<210> SEQ ID NO 17
<211> LENGTH: 120
<212> TYPE: PRT
<213> ORGANISM: Artificial Sequence
<220> FEATURE:
<223> OTHER INFORMATION: Synthetic

<400> SEQUENCE: 17

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Gly Ser Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asn Tyr Phe Val Glu Tyr Phe Gln Tyr Trp Gly Gln
            100                 105                 110

Gly Thr Leu Val Thr Val Ser Ser
            115                 120

<210> SEQ ID NO 18
<211> LENGTH: 108
<212> TYPE: PRT
<213> ORGANISM: Artificial Sequence
<220> FEATURE:
<223> OTHER INFORMATION: Synthetic

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Tyr Ile Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Lys Leu Glu Ile Lys
            100                 105

<210> SEQ ID NO 19
<211> LENGTH: 120
<212> TYPE: PRT
<213> ORGANISM: Artificial Sequence
<220> FEATURE:
<223> OTHER INFORMATION: Synthetic

```
<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Ser Met Asn Trp Val Arg Gln Ala Pro Gly Lys Gly Leu Glu Trp Val
        35                  40                  45

Ser Ser Ile Ser Gly Gln Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Asn Tyr Tyr Val Glu Tyr Phe Gln Tyr Trp Gly Gln
            100                 105                 110

Gly Thr Leu Val Thr Val Ser Ser
            115                 120

<210> SEQ ID NO 20
<211> LENGTH: 108
<212> TYPE: PRT
<213> ORGANISM: Artificial Sequence
<220> FEATURE:
<223> OTHER INFORMATION: Synthetic

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Tyr Ile Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Thr Asp Ser Pro
            85                  90                  95

Ile Thr Phe Gly Gln Gly Thr Lys Leu Glu Ile Lys
            100                 105
```